US012122731B2

(12) United States Patent
Abotaleb et al.

(10) Patent No.: US 12,122,731 B2
(45) Date of Patent: Oct. 22, 2024

(54) SYSTEM AND METHOD FOR LOW-COST METHANE UPGRADING TO ADDED-VALUABLE PRODUCTS

(71) Applicant: Qatar Foundation for Education, Science and Community Development, Doha (QA)

(72) Inventors: Ahmed Abotaleb, Doha (QA); Giovanni Scabbia, Doha (QA); Alessandro Sinopoli, Doha (QA)

(73) Assignee: QATAR FOUNDATION FOR EDUCATION, SCIENCE AND COMMUNITY DEVELOPMENT, Doha (QA)

( * ) Notice: Subject to any disclaimer, the term of this patent is extended or adjusted under 35 U.S.C. 154(b) by 101 days.

(21) Appl. No.: 17/374,247

(22) Filed: Jul. 13, 2021

(65) Prior Publication Data

US 2022/0017434 A1    Jan. 20, 2022

Related U.S. Application Data

(60) Provisional application No. 63/051,653, filed on Jul. 14, 2020.

(51) Int. Cl.
    *C07C 1/32*    (2006.01)
    *B01D 3/00*    (2006.01)
    (Continued)

(52) U.S. Cl.
    CPC .............. *C07C 1/322* (2013.01); *B01D 3/007* (2013.01); *B01D 3/14* (2013.01); *B01J 19/0013* (2013.01);
    (Continued)

(58) Field of Classification Search
    CPC ........ B01D 3/007; B01D 3/14; B01J 19/0013; B01J 19/0033; B01J 19/245; B01J 21/04; B01J 2219/0004; B01J 2219/00103; B01J 2219/00159; B01J 23/04; B01J 23/42; B01J 23/883; B01J 29/40; B01J 35/0006; C01B 2203/0277; C01B 2203/062; C01B 2203/107; C01B 2203/1241;
    (Continued)

(56) References Cited

U.S. PATENT DOCUMENTS 7,659,437 B2    2/2010    Iaccino et al.
7,728,186 B2    6/2010    Iaccino et al.
(Continued)

OTHER PUBLICATIONS

Yu et al. "Catalytic synthesis of methanethiol and its conversion to light olefins" [Phd Thesis 1 (Research TU/e / Graduation TU/e), Chemical Engineering and Chemistry] Feb. 12, 2020 (Year: 2020).*
(Continued)

*Primary Examiner* — Sharon Pregler
(74) *Attorney, Agent, or Firm* — K&L Gates LLP

(57) ABSTRACT

The present disclosure is generally directed to a new and innovative system, process and method that utilize a new "non-oxygen type of oxidizers" process for methane ($CH_4$) upgrading to value-added products such as olefins and aromatics (i.e., benzene, toluene and xylene (BTX)) etc. and further removing toxic impurities such as sulphur-containing compounds (i.e. $H_2S$) by using the sulphur as a source of radical.

17 Claims, 12 Drawing Sheets

(51) Int. Cl.

| | | |
|---|---|---|
| *B01D 3/14* | (2006.01) | |
| *B01J 19/00* | (2006.01) | |
| *B01J 19/24* | (2006.01) | |
| *B01J 21/04* | (2006.01) | |
| *B01J 23/04* | (2006.01) | |
| *B01J 23/42* | (2006.01) | |
| *B01J 23/883* | (2006.01) | |
| *B01J 29/40* | (2006.01) | |
| *C01B 3/26* | (2006.01) | |
| *C01B 32/75* | (2017.01) | |
| *C07C 319/06* | (2006.01) | |

(52) U.S. Cl.
CPC ......... *B01J 19/0033* (2013.01); *B01J 19/245* (2013.01); *B01J 21/04* (2013.01); *B01J 23/04* (2013.01); *B01J 23/42* (2013.01); *B01J 23/883* (2013.01); *B01J 29/40* (2013.01); *C01B 3/26* (2013.01); *C01B 32/75* (2017.08); *C07C 319/06* (2013.01); *B01J 2219/0004* (2013.01); *B01J 2219/00103* (2013.01); *B01J 2219/00159* (2013.01); *C01B 2203/0277* (2013.01); *C01B 2203/062* (2013.01); *C01B 2203/107* (2013.01); *C01B 2203/1241* (2013.01); *C01B 2203/1623* (2013.01); *C07C 2529/40* (2013.01)

(58) Field of Classification Search
CPC ... C01B 2203/1623; C01B 32/75; C01B 3/26; C07C 1/322; C07C 2529/40; C07C 319/06
See application file for complete search history.

(56) References Cited

U.S. PATENT DOCUMENTS

| | | |
|---|---|---|
| 7,977,519 B2 | 7/2011 | Iaccino et al. |
| 8,138,384 B2 | 3/2012 | Iaccino et al. |
| 8,921,625 B2 | 12/2014 | Gadewar et al. |
| 9,856,425 B2 | 2/2018 | Ward et al. |
| 2016/0096168 A1 | 4/2016 | Sangar et al. |
| 2017/0101352 A1* | 4/2017 | Marker ................ C10G 69/126 |

OTHER PUBLICATIONS

Niziolek, et al.; "Production of benzene, toluene, and xylenes from natural gas via methanol: Process synthesis and global optimization"; AICHE; 2016; (26 pages).

* cited by examiner

SYSTEM AND METHOD FOR LOW-COST METHANE UPGRADING TO ADDED-VALUABLE PRODUCTS

PRIORITY CLAIM

This application claims the benefit of and priority to, U.S. Provisional Patent Application No. 63/051,653, filed on Jul. 14, 2020, the entire contents of this application are incorporated herein by reference in its entirety for all purposes.

TECHNICAL FIELD

The present disclosure generally relates to a system and method for upgrading methane ($CH_4$) to value-added products such as olefins and aromatics (i.e., benzene, toluene and xylene (BTX)) etc. by utilizing a new "non-oxygen type of oxidizers" process and further for removing toxic impurities such as sulphur-containing compounds (i.e. $H_2S$) by using the sulphur as a source of radical.

SUMMARY

The following summary is provided to facilitate an understanding of some of the innovative features unique to the aspects disclosed herein, and is not intended to be a full description. A full appreciation of the various aspects can be gained by taking the entire specification, claims, abstract and drawings as a whole.

In various aspects, the present disclosure provides a system, process and method for converting methane ($CH_4$) to value-added products, especially higher hydrocarbons including olefins and aromatic hydrocarbons such as benzene, toluene and xylene, through low-cost techniques such as utilizing a new "non-oxygen type of oxidizers" process. The present disclosure also provides a system, process and method for further removing toxic impurities from the resulted value-added products, such as sulphur-containing compounds (i.e. $H_2S$), by using the sulphur as a source of radical.

In an aspect, the present disclosure provides a process for converting methane ($CH_4$) to higher hydrocarbons including olefins and aromatic hydrocarbons, the process comprising: (i) supplying a first feedstock comprising methane, hydrogen sulfide ($H_2S$), and a first catalytic material to a first reactor; (ii) operating the first reactor under a first reaction condition effective to convert at least a portion of the methane and hydrogen sulfide to carbon disulfide ($CS_2$) and hydrogen ($H_2$); (iii) supplying a second feedstock comprising the resulted carbon disulfide ($CS_2$) and hydrogen ($H_2$) from step (ii) and a second catalytic material to a second reactor; (iv) operating the second reactor under a second reaction condition effective to convert at least a portion of the carbon disulfide ($CS_2$) and hydrogen ($H_2$) to methanethiol ($CH_3SH$) and hydrogen sulfide ($H_2S$); (v) feeding a third feedstock comprising the resulted methanethiol ($CH_3SH$) from step (iv) and a third catalytic material to a third reactor; (vi) operating the third reactor under a third reaction condition effective to convert at least a portion of the methanethiol ($CH_3SH$) to produce the higher hydrocarbons.

In an embodiment, the aromatic hydrocarbons include benzene, toluene and xylene, and optionally naphthalene.

In an embodiment, the first feedstock may further comprise liquid sulphur ($S_8$). In an embodiment, the first feedstock comprises recycled methane and hydrogen sulfide ($H_2S$), and/or makeup methane.

In an embodiment, the first feedstock is mixed together at a slightly positive pressure such as about 1-10 bar or 1-3 bar and at a temperature of 10-100° C. or about 25-50° C.

In an embodiment, the first catalytic material may comprise a $Pt/Al_2O_3$ catalyst. In an embodiment, the first reaction condition may comprise heating the first reactor to a temperature in a range of about 500-1200° C., about 800-1000° C., about 850-950° C., or about 900° C.; and/or applying a pressure of about the standard atmosphere pressure, about 0.8-20 bar, about 1-10 bar, about 1-6, about 1-5 bar, or about 1-3 bar. In an embodiment, an outlet temperature of the first reactor is in a range of about 300-1000° C., about 500-900° C., about 600-800° C., about 650-750° C., about 700-730° C., or about 711° C.

In an embodiment, the conversion of the methane and $H_2S$ to carbon disulfide ($CS_2$) and hydrogen ($H_2$) in the first reactor has a high conversion rate of at least 70%, at least 80%, at least 90%, at least 95%, at least 99%, or about 100%, and a selectivity of the conversation to $CS_2$ is at least 70%, at least 80&, at least 90%, at least 95%, at least 99%, or about 100%.

In an embodiment, the second catalytic material may comprise a $K_2O/NiMo/Al_2O_3$ catalyst. In an embodiment, the conversion of the carbon disulfide ($CS_2$) and hydrogen ($H_2$) to methanethiol ($CH_3SH$) and hydrogen sulfide ($H_2S$) in the second reactor has a high conversion rate of at least 60%, at least 70%, at least 80%, at least 85%, at least 86%, about 86.94%, or in a range of about 60-100%, about 80-90%, or about 84-88%. In an embodiment, the second feedstock comprises additional hydrogen ($H_2$) other than the resulted hydrogen ($H_2$) from the first reactor. With the additional hydrogen ($H_2$), the conversion rate of the carbon disulfide ($CS_2$) and hydrogen ($H_2$) to methanethiol ($CH_3SH$) and hydrogen sulfide ($H_2S$) in the second reactor is increased to at least 80%, at least 85%, at least 90%, at least 95%, at least 98%, at least 99%, or about 100%.

In an embodiment, the second reaction condition may comprise heating the second reactor to a temperature in a range of about 100-800° C., about 150-500° C., about 250-300° C., or about 250° C.; and/or applying a pressure of about the standard atmosphere pressure, about 0.8-20 bar, about 1-10 bar, about 1-8 bar, about 1-6 bar, about 1-5 bar, or about 1-3 bar. The outlet temperature of the second reactor is about 200-700° C., about 300-600° C., about 400-500° C., or about 420-450° C., or about 434° C.

In an embodiment, the third catalytic material is a protonic zeolites H-ZSM-5 (Si/Al 15) catalyst. In an embodiment, the third reaction condition may comprise heating the third reactor to a temperature in a range of about 100-500° C., about 150-400° C., about 250-350° C., or about 300° C.; and/or applying a pressure of about the standard atmosphere pressure, about 0.8-20 bar, about 1-10 bar, about 1-8 bar, about 1-6 bar, about 1-5 bar, or about 1-3 bar. The outlet temperature of the third reactor is about 100-500° C., about 150-400° C., about 200-350° C., or about 250-300° C., or about 287° C.

In an embodiment, the conversion of the methanethiol ($CH_3SH$) to the higher hydrocarbons in the third reactor has a high conversion rate of at least 50%, at least 60%, at least 70%, at least 80%, at least 85%, at least 90%, in a range of about 85-100%, about 90-98%, about 90-95%, or about 93%.

In an embodiment, the first feedstock may comprise liquid sulphur ($S_8$). With the increase of the amount of the liquid sulfur, the reaction temperatures of the first, second and third reactors can be reduced.

In another aspect, the present disclosure provides a process for converting methane ($CH_4$) to higher hydrocarbons including olefins and aromatic hydrocarbons as discussed herein above and elsewhere in the present disclosure, and further for recovering heat generated during the process. The process further comprises recovering the heat generated in the first, second and third reactors during the process.

In an embodiment, the process further comprises: supplying the first feedstock comprising methane, hydrogen sulfide ($H_2S$), and a first catalytic material to a first economizer to be preheated to reach a temperature in a range of about 50-1000° C., about 100-900° C., about 100-800° C., about 200-700° C., or about 250-900° C. before supplying to the first reactor.

In an embodiment, the process comprises: supplying the preheated first feedstock from the first economizer to a first reactor which is heated by a fired heater with external fuel to a temperature in a range of 500-1200° C., about 800-1000° C., about 850-950° C., or about 900°, and operating the first reactor under the first reaction condition effective to convert at least a portion of the methane and hydrogen sulfide to carbon disulfide ($CS_2$) and hydrogen ($H_2$).

In an embodiment, the process further comprises: supplying the second feedstock comprising the resulted carbon disulfide ($CS_2$) and hydrogen ($H_2$) from step (ii) and the second catalytic material to a second economizer before supplying to the second reactor. In an embodiment, the process further comprises: supplying a water to the second economizer; conducting a heat exchange in the second economizer to reduce the temperature of the second feedback down to a range of about 100-800° C., about 150-500° C., about 250-300° C., or about 250° C.; and to recover the heat from the second feedstock to heat up a water to form a steam.

In an embodiment, the process comprises: supplying the second feedstock with reduced temperature from the second economizer to the second reactor; and operating the second reactor under the second reaction condition effective to convert at least a portion of the carbon disulfide ($CS_2$) and hydrogen ($H_2$) to methanethiol ($CH_3SH$) and hydrogen sulfide ($H_2S$).

In an embodiment, the process further comprises: supplying the third feedstock comprising the resulted methanethiol ($CH_3SH$) from step (iv) and the third catalytic material to a third economizer for a heat exchange before feeding to the third reactor. In an embodiment, the process further comprises: supplying water to the third economizer; and conducting the heat exchange between the third feedstock and the water to reduce the temperature of the third feedstock to a range of 100-500° C., about 150-400° C., about 250-350° C., or about 300° C., and to heat up the water to form a steam.

In an embodiment, the process comprises: supplying the third feedstock with reduced temperature from the third economizer to the third reactor; and operating the third reactor under the third reaction condition effective to convert at least a portion of the methanethiol ($CH_3SH$) to produce the higher hydrocarbons.

In an embodiment, the process further comprises: supplying a fourth feedstock comprising the resulted higher hydrocarbons from the third reactor to a fourth economizer for a heat exchange to form a final reaction mixture. In an embodiment, the process further comprises supplying water to the fourth economizer; and conducting a heat exchange between the fourth feedstock from the third reactor and the water to reduce the temperature of the fourth feedstock to a range of about 25-500° C., about 50-300° C., about 25-200° C., or about 25-150° C., and to heat up the water to a steam.

In an embodiment, the process further comprises supplying the resulted steam from the second, third and fourth economizers to the first economizer to pre-heat the first feedstock to up to 1000° C., or up to about 900° C. The steam generated from the second, third and/or fourth economizers may be low-pressure steam.

In an embodiment, the second feedstock comprises impurities, unreacted methane, possibly unreacted hydrogen sulfide, and possibly by-products. In an embodiment, the third feedstock comprises unreacted methane, unreacted carbon disulfide ($CS_2$), unreacted hydrogen ($H_2$), and possibly by-products. The fourth stock comprises methane, hydrogen sulfide, carbon disulfide ($CS_2$), and possibly small amount of hydrogen gas, methanethiol ($CH_3SH$), and possibly by-products. In an embodiment, the final reaction mixture may comprise methane, hydrogen sulfide, carbon disulfide ($CS_2$), and possibly by products and small amount of hydrogen gas, methanethiol ($CH_3SH$) and liquid sulphur.

In another aspect, the present disclosure provides a process for removing impurities, methane and hydrogen sulfide from the resulted higher hydrocarbons and optionally for recycling the methane and hydrogen sulfide to the first economizer. The process comprises: supplying the final reaction mixture to a propane cycle; and separating the final reaction mixture into bottom products and overhead products, wherein the final reaction mixture may comprise the higher hydrocarbons, methane, hydrogen sulfide, by products, and possibly one or more of carbon disulfide ($CS_2$), hydrogen gas, methanethiol ($CH_3SH$), and liquid sulphur, wherein the bottom products at the bottom of the propane cycle comprises higher hydrocarbons including olefins and benzene, toluene and xylene, and optionally naphthalene, wherein the overhead products of the propane cycle comprises methane and hydrogen sulfide.

In an embodiment, the process further comprises: supplying the overhead products comprising methane and hydrogen sulfide to an acid remover unit to remove at least a portion of the hydrogen sulfide to obtain a recovered mixture comprising recovered methane and recovered hydrogen sulfide; and recycle the recovered mixture comprising back to the first economizer or to the first reactor.

In another aspect, the present disclosure provides a system for converting methane to higher hydrocarbons including olefins and aromatic hydrocarbons, the system comprising: a reaction unit comprising a first reactor, a second reactor and a third reactor; and optionally one or more of a heat integration system; a separation unit; and a recycling unit.

In an embodiment, the reaction unit comprises: (i) a first reactor configured to receive a first feedstock, the first reactor comprising a first catalytic material formulated for converting at least a portion of the methane and hydrogen sulfide to carbon disulfide ($CS_2$) and hydrogen ($H_2$) to form a first resulted mixture comprising the carbon disulfide ($CS_2$) and the hydrogen ($H_2$); (ii) a second reactor fluidly connected to the first reactor to receive the first resulted mixture, the second reactor comprising a second catalytic material formulated for converting at least a portion of the carbon disulfide ($CS_2$) and hydrogen ($H_2$) to methanethiol ($CH_3SH$) and hydrogen sulfide ($H_2S$) to form a second resulted mixture comprising the methanethiol ($CH_3SH$) and the hydrogen sulfide ($H_2S$); and (iii) a third reactor fluidly connected to the second reactor to receive the second resulted mixture, the third reactor comprising a third catalytic material formulated for converting at least a portion of the methanethiol ($CH_3SH$) to the higher hydrocarbons to produce a third resulted mixture comprising the higher hydrocarbons.

In an embodiment, the heat integration system comprises a first economizer configured to receive and preheat a first feedstock that feeds into the economizer, the first economizer is configured to be fluidly connected to the first reactor to supply the preheated first feedstock to the first reactor.

In an embodiment, the heat integration system further comprises a fired heater configured to heat the first reactor.

In an embodiment, the heat integration system further comprises a second economizer fluidly connected to the first reactor to receive and cool down the first resulted mixture from the first reactor; and fluidly connected to the second reactor configured to supply the cooled first resulted mixture to the second reactor.

In an embodiment, the heat integration system further comprises a third economizer fluidly connected to the second reactor to receive and cool down the second resulted mixture from the second reactor; and fluidly connected to the third reactor configured to supply the cooled second resulted mixture to the third reactor.

In an embodiment, the heat integration system further comprises a fourth economizer fluidly connected to the third reactor to receive and cool down the third resulted mixture from the third reactor to form a final reaction mixture comprising the resulted higher hydrocarbons. The final reaction mixture comprises by-products, methane and hydrogen sulfide, and one or more of the carbon disulfide ($CS_2$), hydrogen ($H_2$), methanethiol ($CH_3SH$) and liquid sulfur.

In an embodiment, the second, third and/or fourth economizers are configured to receive water and generate water steam such as low-pressure water steam to recover the heat energy generated during the reactions in the first, second and third reactors.

In an embodiment, the first economizer is configured to receive the steam from the second, third and fourth economizers to preheat the first feedstock.

In an embodiment, the separation unit comprises a propane cycle fluidly connected to the fourth economizer or the third reactor, configured to receive and separate the final reaction mixture from the fourth economizer or the third resulted mixture from the third reactor into bottom products and overhead products, the bottom products comprise the higher hydrocarbons such as olefins, benzene, toluene and xylene and optionally naphthalene, and wherein the overhead products comprise methane and hydrogen sulfide. In an embodiment, the propane cycle comprises a heat exchanger, a compressor, one or more control valves and a flash vessel.

In an embodiment, the recycling unit comprises an acid gas removal unit configured to receive the overhead products from the propane cycle and to remove at least a portion of the hydrogen sulfide to form a recovered mixture comprising the recovered methane and the recovered hydrogen sulfide. In an embodiment, the system is further configured to recycle the recovered mixture from the acid gas removal unit to the first economizer.

The present disclosure provides a new and innovative system and method that utilize a new "non-oxygen type of oxidizers" process for methane ($CH_4$) upgrading to value-added products such as olefins and aromatics (i.e., benzene, toluene and xylene (BTX)) etc. and further removing toxic impurities such as sulphur-containing compounds (i.e. $H_2S$) by using the sulphur as a source of radical.

In one aspect, the present disclosure provides a novel system for converting methane to value-added products, specifically olefins and aromatics such as benzene, toluene and xylene (BTX) through low-cost techniques and to remove toxic impurities such as hydrogen sulfide ($H_2S$).

In various aspect, the system for converting methane ($CH_4$) to benzene, toluene and xylene (BTX) and for removing a sulphur-containing toxic impurity, the system comprising a reaction section, wherein the reaction section comprises at least three reactors including a first reactor, a second reactor and a third reactor, each of the at least three reactors comprises a different catalyst system, different feedstock and different products, the feedstock of the first reactor comprises recycled methane ($CH_4$) and hydrogen sulfide ($H_2S$), makeup methane and liquid sulfur ($S_8$), wherein the first reactor is connected to the second reactor and the second reactor is further connected to the third reactor through connection pipes, and the reaction section is configured to convert the products and the unconverted feedstock of the first reactor to the second reactor, and further to convert the products and the unconverted feedstock of the second reactor to the third reactor through the connection pipes.

In an embodiment, the system further comprises a heat integration system, a separation unit and an acid gas removal (AGR) unit wherein the heat integration system is configured to be integrated with the reaction section, the separation unit is configured to connect to reaction section, and the acid gas removal unit is configured to connect to the separation unit.

In an embodiment, the sulphur-containing toxic impurity comprises hydrogen sulfide ($H_2S$).

In an embodiment, the catalyst system of the first reactor comprises $Pt/Al_2O_3$ catalyst.

In an embodiment, the catalyst system of the second reactor comprises $K_2O/NiMo/Al_2O_3$ catalyst.

In an embodiment, the catalyst system of the third reactor comprises a protonic zeolites H-ZSM-5 (Si/Al 15) solid acid catalyst.

In an embodiment, the heat integration system comprises a waste-heat-recovery system including a integration of Economizers 1 to 4 with the reaction section.

In an embodiment, the separation unit comprises a Propane cycle for physical separation of BTX and unconverted $CH_4$ and $H_2S$.

In an embodiment, the separation unit further comprises at least one air cooler.

In an embodiment, the acid gas removal (AGR) unit is configured to recycle unconverted $CH_4$ and $H_2S$ at the desired ratios of about 1:1, about 10:1 or about 20:1 and to purge excess $H_2S$ from the AGR unit.

In various aspect, the present disclosure provides a method utilizing a "non-oxygen type of oxidizers" process for converting methane ($CH_4$) to value-added products benzene, toluene and xylene (BTX) and for removing sulphur-containing toxic impurity, the method comprising: performing at least three chemical reactions including a first reaction in a first reactor, a second reaction in a second reactor, and a third reaction in a third reactor in a reaction section, wherein each of the at least three reactions is conducted under a different catalyst system and different feedstock, and produces different products, wherein the feedstock of the first reaction comprises recycled methane ($CH_4$) and hydrogen sulfide ($H_2S$), makeup methane ($CH_4$) and liquid sulfur ($S_8$), wherein the feedstock of the second reaction comprises the products and unconverted feedstock of the first reaction, wherein the feedstock of the third reaction comprises the products and the unconverted feedstock of the second reaction, and wherein the products of the third reaction comprise at least benzene, toluene and xylene (BTX).

In an embodiment, the sulphur-containing toxic impurity comprises hydrogen sulfide ($H_2S$).

In an embodiment, the catalyst system of the first reaction comprises $Pt/Al_2O_3$ catalyst.

In an embodiment, the catalyst system of the second reaction comprises $K_2O/NiMo/Al_2O_3$ catalyst.

In an embodiment, the catalyst system of the third reaction comprises a protonic zeolites H-ZSM-5 (Si/Al 15) solid acid catalyst.

In an embodiment, the method further comprises feeding the products and the unconverted feedstock of the third reaction to a separation unit; and separating the BTX from the unconverted methane ($CH_4$) and hydrogen sulfide ($H_2S$) through the separation unit.

In an embodiment, the separation unit comprises a propane cycle and at least one air cooler.

In an embodiment, the method further comprises recycling unconverted $CH_4$ and $H_2S$ at the desired ratios of about 1:1, about 10:1 or about 20:1 using an acid gas removal (AGR) unit and further purging excess $H_2S$ from the AGR unit.

In an embodiment, the method further comprises integrating a heat integration system with the reaction section, wherein the heat integration system comprises Economizers 1 to 4.

In an embodiment, the method further comprises preheating the feedstock of the first reaction section using a Economizer 1; and preheating the first reactor to about 900° C.

In an embodiment, the process flow diagram for low-cost methane upgrading to more valuable products is described in FIG. 1. As shown in FIG. 1, the system may comprise a reaction section with multiple reactors (such as three reactors) each using different specifically designed catalysts and reaction conditions respectively as shown in Table 2 below. The system may further comprise a heat integration system, a separation unit and an acid gas removal unit.

In an embodiment, as shown in FIG. 1, the heat integration system is the waste-heat-recovery system including the integration of Economizers 1 to 4 with the reaction section. The heat integration system can reduce the fuel gas required to heat the feedstock up to the reaction temperatures such as 900° C. in Reactor A. This heat integration system and process save 61% of the fuel gas to heat the reactants up to the reaction temperatures which corresponds to a saving of $36/Ton of BTX produced.

In an embodiment, as shown in FIG. 1, the separation unit uses physical separation instead of the conventional distillation column for the separation of BTX, naphthalene, $CH_4$ and $H_2S$. The physical separation uses Propane cycle as a refrigerant to condense the BTX as a bottom product and release the non-condensable gases ($CH_4$ and $H_2S$) as a top product. The Propane cycle can achieve high BTX separation and recovery. The separation unit further includes air coolers instead of a cooling tower to further reduce the product cost.

In an embodiment, as shown in FIG. 1, the acid gas removal (AGR) unit is included to recycle unconverted $CH_4$ and $H_2S$ at the desired ratios of 1:1, 10:1 or 20:1 and to purge excess $H_2S$ from the AGR unit. The inventors found that this step reduces the feedstock cost and unit production cost, minimizes waste, and increases the unit profit.

In another aspect, the present disclosure provides a novel method utilizing a new "non-oxygen type of oxidizers" process for converting methane ($CH_4$) to value-added products, specifically olefins and aromatics such as benzene, toluene and xylene (BTX) through low-cost techniques and to remove toxic impurities such as hydrogen sulfide ($H_2S$). In an embodiment, as shown in FIG. 1, the method may comprise performing three major chemical reactions each of which is conducted in one of the three Reactors A to C respectively, and each chemical reaction has its specifically designed catalysts and reaction conditions as shown in Table 2 below.

The presently disclosed process, system and method are advantageous over conventional methods (such as Naphtha to BTX method, oxidative coupling of methane (OCM) method, methane aromatization method and mercaptans to BTX method) in that the presently disclosed system and method utilize a low cost process which generates minimal waste and further do not generate environmentally sensitive carbon oxides.

The features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the claimed subject matter.

These and other features are disclosed in greater detail in the accompanying figures and the Detailed Description below.

BRIEF DESCRIPTION OF THE DRAWINGS

Some embodiments of the present disclosure, and ways of making and of using one or more embodiments of the present disclosure, are described in detail herein and by way of example, with reference to the several views of the accompanying drawing (which are not necessarily drawn to scale with regard to any internal or external structures shown) and in which like reference characters designate like elements throughout the several views, and in which.

DETAILED DESCRIPTION

Figure 1:
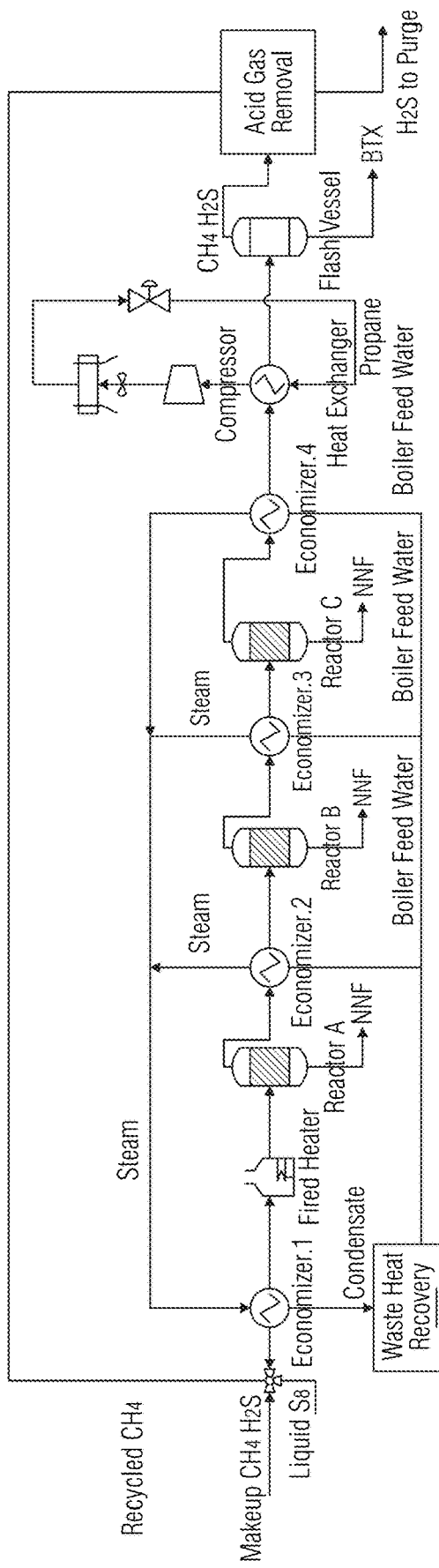
FIG. 1 illustrates an example process flow diagram for low-cost methane upgrading to more valuable products, according to an aspect of the present disclosure.

Typically, Benzene, Toluene and Xylene (BTX) products are produced through catalytic reforming of naphtha. This takes higher order hydrocarbons, usually six to twelve carbon hydrocarbons and reforms them from linear type hydrocarbons into ring type hydrocarbons using a catalytic reformer [1]. Naphtha prices are currently marketed at around $500 per ton, which is more expensive than methane ($CH_4$) and slightly cheaper than the BTX products derived from its reforming [2]. Currently this process yields 50-55% toluene. 30-35% xylenes and only about 10-15% benzene [3].

Benzene is the most widely used aromatic petrochemical in the industrial processes. Its price has been increasing over the past five years [4]. Toluene finds the largest industrial use among BTX. Its selling price has been directly linked with the crude oil as the majority of BTX production is via crude oil cracking. Thus, it is predicted that production outages and political tensions are likely to keep the price of toluene volatile in the foreseeable future. p-Xylene is the most valuable product per pound that is created in the production of BTX. The demand in the market for p-xylene is highly correlated with the demand for PET polyesters and their derived products. Tecnon OrbiChem, a UK-based consulting firm, estimates world consumption to increase by 7% per year.

With a market for BTX valued at $80.8 billion in sales per year, the three largest competitors in BTX industry are Exxon Mobil Corporation and The Dow Chemical Company, followed by Anellotech Inc., which is another smaller competitor that aims to produce BTX products from renewable sources.

Exxon Mobil Chemical is the largest North American producer of benzene and toluene and the second-largest producer of mixed xylene—holding an overall market share of 3.0%. Its sales are estimated at $2.45 billion per year and it is expected to grow at an annual rate of 15.8%.

The Dow Chemical Company holds an overall BTX market share of 2.6%. Its sales are estimated at $2.1 billion per year.

Anellotech Inc. has developed a clean technology platform to inexpensively produce BTX from renewable biomass. It is expected that their products will be cheaper when compared to petroleum derived counterparts, while providing identical benefit.

Currently, there are different approaches to produce olefins and aromatics (benzene, toluene and xylene) from different feedstock. However, these approaches suffer from one or more operational and scale up issues and high cost. Accordingly, improved systems and methods are desired for producing olefins and aromatics (benzene, toluene and xylene) with reduced cost.

The present disclosure provides a novel and innovative systems and methods to convert methane ($CH_4$) to value-added products, specifically olefins and aromatics (Benzene, Toluene and Xylene) through low-cost techniques by utilizing a new "non-oxygen type of oxidizers" process; as well as to remove toxic impurities such as sulphur-containing compounds (i.e. $H_2S$) by using the sulphur as a source of radical.

The present inventors have identified several approaches to convert methane to added-valuable products. These approaches are detailed below.

Because of the large amount of $CH_4$ that is available from natural sources, it is strongly desired to develop processes for direct and indirect conversion of this substance into value-added products. Technologies deriving from these processes could represent a huge opportunity for Qatar where natural gas represents the first largest source with proven recoverable resources at 900 Trillion SCF, 2016.

Oxidative Coupling of Methane Method

Among the methods devised for direct conversion of $CH_4$ to value-added chemicals, oxidative coupling of methane ($CH_4$) (OCM) to produce $C_2$ products such as $C_2H_6$ and $C_2H_4$, with $C_2H_4$ representing ~50% of the hydrocarbon feedstock for the chemical industry, is the most popular. The OCM catalytic reaction was first reported by Keller and Bhasin in 1982 [5] and has attracted significant attention over the years in order to gain a deeper understanding of its fundamentals with the aim of making the OCM catalytic process commercially viable. Although OCM is not thermodynamically limited because the overall reaction is exothermic and exergonic, it is kinetically hindered and there is still needs for better performing catalysts to make OCM industrially viable [6].

The OCM catalytic reaction faces selectivity issues since the free energy change of the OCM reaction is about −154 kJ/mol at 800° C. while that of complete oxidation of $CH_4$ into $CO_2$ is about −801 kJ/mol [6]. In addition, the OCM catalytic process involves both heterogeneous and homogeneous reaction steps that further complicate its understanding. Fundamentally, the process involves the activation of a C—H bond of $CH_4$ to form gaseous methyl radicals ($CH_3$•) via a heterogeneous catalytic step followed by a gas phase homogeneous recombination step of the $CH_3$• radicals to yield $C_2H_6$. The $C_2H_6$ can further undergo oxidative dehydrogenation over the same catalyst to form the highly desired $C_2H_4$ product. It has been reported that OCM holds the greatest potential as the most cost-effective and environmentally friendly method of converting $CH_4$ to chemicals compared to the energy and capital-intensive indirect routes [6].

Methane Aromatization Method

Another promising gas-to-liquid (GTL) process is based on the aromatization of methane [7]. From the first study of Wang, research has been extensively carried out on this subject [8]. However, achieving a technologically viable process involves improvements in the catalyst, increases in conversions and yields and stability of the process.

New processes have been proposed for methane conversion to BTX by typically employing Metal/zeolite catalysts for benzene selectivity [9a]. Generally, Mo/ZSM-5 catalyst is chosen due to the largest combined selectivity to BTX type products and the lack of methane converted to Coke. Side products of this process include diatomic hydrogen and naphthalene. The biggest obstacle in this process lies in the large recycle stream due to the low conversion of methane by the catalyst (usually below 10%), with the recycle stream accounting for about 90% of the methane being fed into the reactor [9b]. Despite this large recycle, the process seems to be a viable option to create benzene and toluene for profit.

Mercaptans to BTX Method

Usually, the treated gas contains minor amounts of contaminants: >2% $CO_2$, 2-4 ppm $H_2S$ and 5-30 ppm total sulfur (mercaptans and carbonyl sulphide). With the increasingly stringent environmental regulations, the technical requirements for further catalytic processes (e.g. syngas fabrication) and the specificities of newly discovered gas deposits with a mercaptan concentration range substantially higher than those hitherto known, the demand for more complete desulfurization is rising. In 2013, the group of Hulea, in collaboration with TOTAL SA, presented a way to catalytically convert $CH_3SH$ and $CH_3SCH_3$ (DMS), on protonic zeolites H-ZSM-5, H-Y and H-ferrierite and above 700 K, to light alkanes ($C_1$-$C_3$), benzene, toluene and xylene. They found that, at 823 K, the $CH_3SH$ conversion is total on H-ZSM-5, and only partial on H-Y and H-ferrierite. These resulted selective to alkanes and produced large quantities of coke. In contrast, much less coke builds up on H-ZSM-5, which was also more selective to aromatics. After calcination, the spent H-ZSM-5 sample recovered the properties of the fresh catalyst [10].

Later, the same group demonstrated the catalytic activity of various H-zeolite/zeotype toward conversion of $CH_3SH$ into $H_2S$ and hydrocarbons (M2TH process). The catalytic activity varied as follows: H-ZSM-5>H-Y>H-FER>H-BEA>H-MOR>H-SAPO-34. In addition, H-ZSM-5 was the most stable catalyst toward deactivation by coke. The effect of the carrier gas (nitrogen or methane) and the role of water on the catalytic behaviour of zeolites were explored under different conditions. Similar performances were obtained using $CH_3SH/N_2$ or $CH_3SH/CH_4$ mixtures, but the amount of coke drastically decreased, and the catalyst lifetime increased when 2% of water was added into the reaction [11].

As briefly mentioned above, mercaptans are of great industrial interest and are very widely used nowadays by the chemical industries, particularly as precursors or starting materials for the synthesis of more complex organic molecules. However, natural gas (NG) treatment is not the only way to isolate mercaptans. Methyl mercaptan is nowadays commonly produced industrially on the tonnage scale from methanol, with more than a few drawbacks associated with this method. In 2014, Arkema France patented a valuable alternative for the preparation of methyl mercaptan [12]. The new method comprised the reaction of methane with hydrogen sulphide ($H_2S$) to form carbon disulphide ($CS_2$) and hydrogen ($H_2$), these two products would further react to yield methyl mercaptan ($CH_3SH$), hydrogen sulphide ($H_2S$) and possibly hydrogen ($H_2$). Then the methyl mercaptan can be isolated and the $H_2S$ can be recycled to further react with methane. Catalyst materials for methyl mercaptan catalytic production generally comprise molybdenum- and potassium-based active component on hydroxyapatite-based supports [13].

Data Science for Catalysis

Understanding and controlling the catalytic reactions are considered big challenges in chemistry and industry. Catalytic reactions typically involve multiple experimental factors and surface chemistries in a complex manner, making it difficult to represent with a comprehensive model. However, the implementation of data science could potentially shine a light and reveal such complex matter within catalysis, as machine learning (ML) can treat multiple factors in high dimensions [14-15].

With machine learning (ML) techniques, any catalytic process can be considered as a multi-dimensional problem. Thanks to this approach, further sophisticated catalyst design and tailored tuning of reaction conditions can be made achievable in principle. The effect of catalytic reaction conditions is usually expressed by the influence and importance of each reaction parameter on the target products by conducting reactions under various conditions, and then either find the optimal experiment conditions empirically or instinctively when the data dimensions becomes high and complex. If the effects of the reaction conditions can be organized and if accurate models can be constructed using machine learning, then it would be possible to survey the information isolating the effects of each reaction parameter and select the optimum reaction conditions from predicted data, even if the range is not investigated through experiments. Here, machine learning is implemented in order to determine the reaction conditions in heterogeneous catalysis [16].

$CH_4$ Conversion.

Catalysts for OCM reactions have been analysed and predicted by several groups using a database consisting of nearly 2000 data sets on catalyst compositions and their performances collected from diverse published data [17]. Very recently, the group of Shimizu and Takigawa reported a statistical analysis and a proposal of novel heterogeneous catalysts for OCM using ML treatment of literature data [18]. This effort led to the development of a novel ML method considering elemental features as input representations instead of inputting catalyst compositions directly. Effective analysis of literature data by ML methods has the capability to provide valuable information. Nevertheless, utilization of literature data has obstacles such as bias from prior published data, low sample counts for many elements, and lack of composition overlaps.

The newly developed method has the potential to guide catalyst design and discovery, including those that promote reactions where limited catalyst composition overlap exists in the given data. The prediction accuracy of this approach is higher than those of conventional methods using catalyst compositions as input. Among various, state-of-the art ML models developed, gradient boosting regression with XGBoost displayed the highest level of performance to predict catalytic performance. In order to determine quantitatively the most important input variables for prediction of the catalytic performance, a feature importance score was also obtained. Moreover, a catalyst optimization procedure that uses ML as "surrogate" models identified the top 20 promising catalyst candidates. This investigation provided fundamental knowledge about catalytic processes. Moreover, it has the potential of being used to identify truly novel heterogeneous catalysts where the reported data are limited and biased because they are very noisy and inconsistent because of variations arising from the use of different instruments, procedures, and platforms.

Currently, $CH_4$ is industrially converted through auto thermal or catalytic steam reforming to form synthesis gas (a mixture of $H_2$ and CO), which then is used for large-scale manufacture of methanol and higher-molecular-weight hydrocarbons. Although these processes are already industrially viable, they suffer from harsh reaction conditions. Thus, better catalysts are needed.

The Yildirim group constructed 5508 experimental data points for steam reforming of $CH_4$ (SRM) using 81 publications appearing between 2004 and 2014 [19]. The database was analyzed using decision trees to extract correlations, heuristics, and trends that are not identifiable using only the naked eye. Analysis of the performance variable showed that Ni, Ru, Rh, and Pt are the most frequently used active metals and that they are normally supported on $Al_2O_3$, $CeO_2$, or $ZrO_2$ employing impregnation methods. In addition, the analysis determined the ranges of catalyst preparation and operational conditions employed that lead to high $CH_4$ conversion. More recently, the same group extracted knowledge for the dry reforming of $CH_4$ (DRM) reaction from literature experimental data employing data mining tools [20]. A database having 5521 data points was constructed from 101 papers reported between 2005 and 2014.

Recently Nguyen et al developed a high throughput screening instrument for enabling an automatic performance evaluation of 20 catalysts in 216 reaction conditions [21]. This tool is based on an oxidative coupling of methane dataset comprised of 12 708 data points for 59 catalysts in three successive operations. Based on a variety of data visualization analysis, important insights into catalysis and catalyst design were successfully extracted. In particular, the simultaneous optimization of the catalyst and reactor design was found to be essential for improving the $C_2$ yield. The consistent dataset allowed the accurate prediction of the $C_2$ yield with the aid of nonlinear supervised machine learning.

The present disclosure is generally directed to a system, process and method for converting methane to added-valuable products, specifically olefins and aromatics (Benzene, Toluene and Xylene) through low-cost techniques, as well as to remove toxic impurities ($H_2S$). This process involves three reactors with three different catalysts, heat integration system, separation unit (propane cycle), and Acid gas removal unit.

The present disclosure is related to Oil & Gas sector and should be considered as a large-scale technology. The expected profit per unit from this technology is $480/Ton-BTX compared to $50/Ton-methane (pipeline export rate for methane). The methane value could increase by ten times thanks to this technology.

In one aspect, the present disclosure provides an example process flow diagram for low-cost methane upgrading to more valuable products as shown in FIG. 1. The mass balance across all the process units are reported in Table 1, and the chemical reactions, catalysts and reaction conditions are shown in Table 2.

The feedstock for Reactor-A consists of recycled methane and $H_2S$, makeup methane and liquid sulfur ($S_8$). The reactants are mixed together at slightly positive pressure and temperature at 25-50° C. Afterwards, the reactants are first preheated in Economizer 1, followed by a fired heater derived with external fuel to elevate the reactor-A reactants to 900° C. Then, Reactor-A downstream at 711° C., will be exchanged in Economizer 2 to generate steam as waste heat recovery. The main products from Reactor-A are $CS_2$ and $H_2$, which are then directed to Reactor-B, where Hydrogen gas reacts with $CS_2$ yielding $CH_3SH$. As, reactor-B downstream recorded 434° C., it will be exchanged with boiler feed water to generate low-pressure steam as waste heat recovery. At this point, the produced $CH_3SH$ is directed to Reactor-C at 300° C. to be converted into BTX, olefins and $CH_4$. Reactor-C downstream products are at 287° C., therefore it will be exchanged in Economizer 4 with boiler feed water to cool down its temperature while generating low-pressure steam as waste heat recovery.

Finally, all the products and by-products are going to be separated in a propane cycle by physical separation, where the bottom products are benzene, toluene, xylene and naphthalene, while the overhead products are $CH_4$ and $H_2S$.

The $CH_4$—$H_2S$ is now directed to acid gas removal unit to remove the excess $H_2S$ and recycle the unreacted $CH_4$—$H_2S$ back to Reactor-A.

TABLE 1

Mass balance of the three reactors, the separation unit and the acid gas removal unit.

| Item | Reactor A | | | Reactor B | | | Reactor C | | |
|---|---|---|---|---|---|---|---|---|---|
| kg/hr | In | Reacted | Out | In | Reacted | Out | In | Reacted | Out |
| $CH_4$ | 1606.8 | 110.07 | 1496.71 | 1496.71 | 0.00 | 1496.71 | 1496.71 | 0.00 | 1653.83 |
| $H_2S$ | 160.68 | 160.68 | 0.00 | 0.00 | 0.00 | 209.49 | 209.49 | 0.00 | 238.05 |
| S | 296.00 | 269.00 | 0.00 | 0.00 | 0.00 | 0.00 | 0.00 | 0.00 | 0.00 |
| $CS_2$ | 16.75 | 0.00 | 538.32 | 538.32 | 488.04 | 70.28 | 70.28 | 0.00 | 70.28 |
| $H_2$ | 0.00 | 0.00 | 37.18 | 37.18 | 37.18 | 0.00 | 0.00 | 0.00 | 0.00 |
| $CH_2SH$ | 11.32 | 0.00 | 11.32 | 11.32 | 0.00 | 307.07 | 307.07 | 285.58 | 21.50 |
| Benzene | 2.37 | 0.00 | 2.37 | 2.37 | 0.00 | 2.37 | 2.37 | 0.00 | 85.58 |
| Toluene | 0.39 | 0.00 | 0.38 | 0.38 | 0.00 | 0.38 | 0.38 | 0.00 | 64.16 |
| Xylene | 0.01 | 0.00 | 0.01 | 0.01 | 0.00 | 0.01 | 0.01 | 0.00 | 12.60 |
| $ArC_{10}$ | 0.00 | 0.00 | 0.00 | 0.00 | 0.00 | 0.00 | 0.00 | 0.00 | 40.38 |

| Item | SEP (Propane Cycle) | | | Acid Gas Removal | | |
|---|---|---|---|---|---|---|
| kg/hr | In | TOP | Bottom | In | Recycled | Flared |
| $CH_4$ | 1653.83 | 1552.96 | 0.87 | 1552.96 | 1552.84 | 0.12 |
| $H_2S$ | 238.05 | 238.05 | 0.89 | 228.16 | 155.06 | 73.11 |
| S | 0.00 | 0.00 | 0.00 | 0.00 | 0.00 | 0.00 |
| $CS_2$ | 70.28 | 18.17 | 52.11 | 18.17 | 15.76 | 2.41 |
| $H_2$ | 0.00 | 0.00 | 0.00 | 0.00 | 0.00 | 0.00 |
| $CH_2SH$ | 21.50 | 11.06 | 10.43 | 11.06 | 11.32 | 0.00 |
| Benzene | 85.58 | 2.31 | 83.22 | 2.31 | 2.37 | 0.00 |
| Toluene | 64.16 | 0.37 | 63.79 | 0.37 | 0.38 | 0.00 |
| Xylene | 12.60 | 0.01 | 12.59 | 0.01 | 0.01 | 0.00 |
| $ArC_{10}$ | 40.38 | 0.00 | 40.38 | 0.00 | 0.00 | 0.00 |

TABLE 2

Chemical reactions, catalysts and reaction conditions involved in the three Reactors A, B and C.

| Compound | Effluent Mass Composition (%) |
|---|---|
| Reactor A: $CH_4 + 2H_2S \rightarrow CS_2 + 4H_2$; Catalyst: $Pt/Al_2O_3$, 1 bar and 900° C. | |
| $CH_4$ | 72.23 |
| $H_2S$ | 0 |
| $CS_2$ | 25.98 |
| $H_2$ | 1.79 |
| Reactor B: $CS_2 + 3H_2 \rightarrow CH_3SH + H_2S$; Catalyst: $K_2O/NiMo/Al_2O_3$, 1 bar and 250° C. | |
| $CS_2$ | 11.98 |
| $H_2$ | 0 |
| $CH_3SH$ | 52.33 |
| $H_2S$ | 35.70 |
| Reactor C: $9CH_3SH \rightarrow 3CH_4 + 9H_2S + BTX$; Solid acid catalyst: Protonic zeolites H-ZSM-5 (Si/Al 15), 1 bar end 300° C. | |
| $CH_2SH$ | 6.94 |
| $H_2S$ | 9.22 |
| $CH_4$ | 18.43 |
| Benzene | 27.60 |
| Toluene | 20.71 |
| Xylene | 4.07 |
| Ar-C10 | 13.03 |

Reactor A: Methane Activation

The first reaction to convert methane and hydrogen sulfide to carbon disulfide ($CS_2$) and hydrogen ($H_2$) in Reactor A can achieve up to 100% conversion rate (complete conversion), and the selectivity of the conversion of the methane and hydrogen sulfide is 100% selectivity to $CS_2$ using the present first catalyst $Pt/Al_2O_3$. The outlet temperature of the Reactor A is about 711° C. Increasing the liquid sulfur content will decrease the reaction temperature Reactor B: Methyl Mercaptan Synthesis The conversion rate of the reaction in Reactor B was recorded 86.94% conversion. Unreacted $CS_2$ will accumulate in the system due to insufficient $H_2$. Adding hydrogen would enhance the synthesis reaction and ensure 100% $CS_2$ conversion to $CH_3SH$. The outlet temperature of Reactor B is about 434° C. as it is an exothermic reaction.

Reactor C: Methyl Mercaptan Conversion

The product distributions of the conversion reactions in the Reactor C are shown in Table. 3. The outlet temperature of Reactor C is about 287° C.

TABLE 3

| Reactor C Conversion and Selectivity | |
|---|---|
| $CH_3SH$ unreacted | 7.00% |
| Benzene | 27.08% |
| Toluene | 20.77% |
| Xylene | 4.10% |
| ArC10 | 13.15% |
| Methane | 18.60% |
| $H_2S$ | 9.30% |

The advantages of the novel and innovative systems and methods of the present disclosure disclosed above are summarized below and for example.

First, the present disclosure provides a low-cost process technology for methane upgrading to olefins and aromatics with only 3.36% methane makeup, while the rest is recycled (See FIG. 1).

Second, the present disclosure introduces a waste-heat-recovery system to reduce the fuel gas required to heat the feedstock up to 900° C. Economizers 1, 2, 3 and 4 were added before and after the reactors A, B and C to allow heat exchanging the process streams with water to generate low-pressure superheated steam and to condition the process streams for the following operations. The superheated steam will be exchanged with the combined feed, recycled stream and liquid-sulfur in a new preheater heat exchanger (Economizer-1). This heat integration saves 61% of the required fuel gas to heat the reactants up to 900° C., which corresponds to a saving of $36/Ton-BTX produced.

Figure 2:
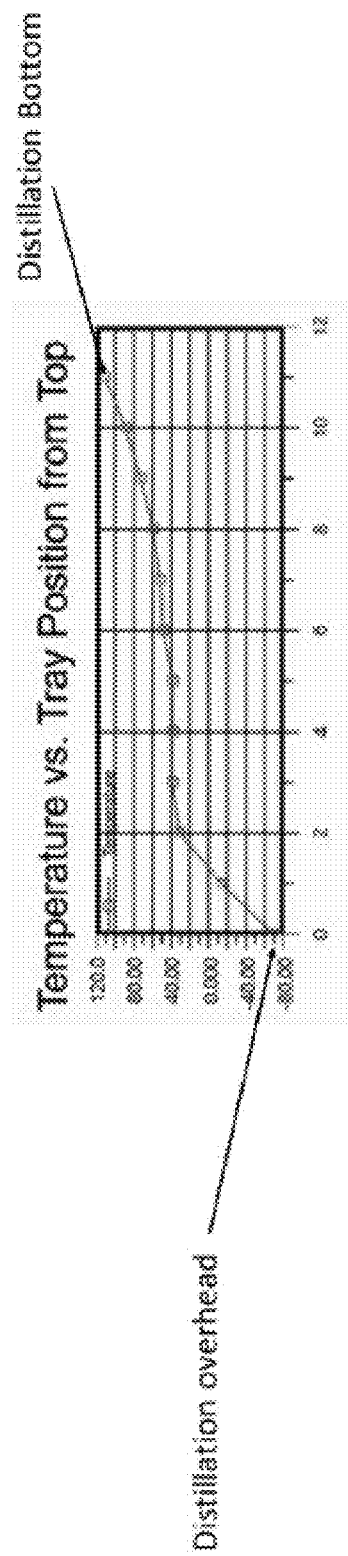
FIG. 2 illustrates an example temperature profile for conventional BTX separation using distillation column, according to an aspect of the present disclosure.

Third, using conventional Distillation column for BTX, naphthalene, $CH_4$ and $H_2S$ separation is not recommended due to the wide temperature difference (−80° C. to 130° C., See FIG. 2.), which would affect the material mechanical properties and thus its lifetime. The Temperature profile for conventional BTX separation using distillation column is described in FIG. 2. Hence, physical separation is here proposed by using Propane cycle as a refrigerant to condense the BTX as a bottom product and release the non-condensable gases ($CH_4$ and $H_2S$) as a top product.

The typical propane cycle is applied without adding economizer nor 2nd compressor. The propane cycle could achieve high BTX separation recovery as shown in Table 4. Moreover, instead of using cooling tower, Air coolers are proposed as the cheapest cooling method and design outlet temperature is set at 57° C. to match Qatar summer/design conditions.

TABLE 4

| Separation Recovery using Propane Cycle | |
|---|---|
| Product | Recovery |
| Benzene | 97.30% |
| Toluene | 99.42% |
| Xylene | 99.90% |
| AR-C10 | 100.00% |
| Total BTX | 98.34% |

Figure 3:
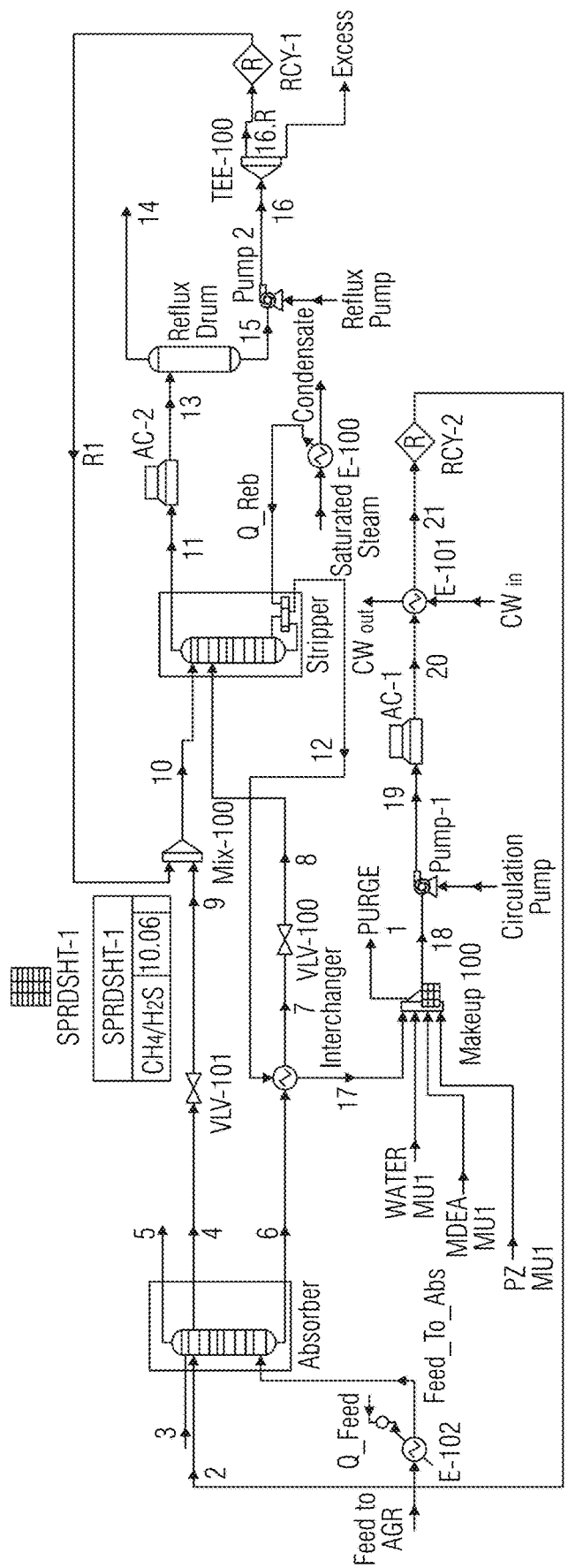
FIG. 3 illustrates an example Acid Gas Removal Process Flow Diagram, according to an aspect of the present disclosure.
Figure 4:
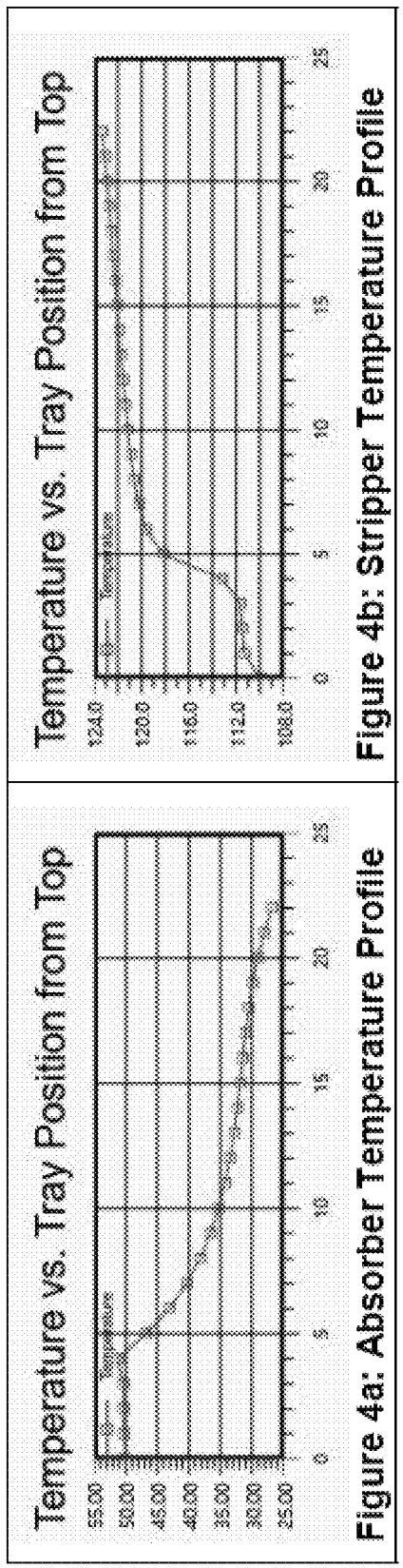
FIG. 4a illustrates an example absorber temperature profile, according to an aspect of the present disclosure.
FIG. 4b illustrates an example stripper temperature profile, according to an aspect of the present disclosure.

Fourth, $H_2S$ removal is required since the $CH_4/H_2S$ ratio is 6.8:1 directly after the aromatics separation. Therefore, to recycle unconverted $CH_4$ and $H_2S$ at the desired ratios about 1:1 to about 20:1, such as about 10:1 or 20:1. An Acid Gas Removal (AGR) unit was added (see FIGS. 3, 4a and 4b). Accordingly, the low-cost process technology for methane upgrading to olefins and aromatics generate only 3.36% methane makeup, while the rest is recycled (see FIG. 1), excess $H_2S$ will be purged from AGR unit.

This step reduces the feedstock cost and unit production cost as well as increasing the unit profit. Using AMP as solvent, $H_2S$ Loading records 0.5534 mol-$H_2S$/mol-Amine. In addition, Claus process could be integrated to recover sulfur rather than flaring/incinerating the stripped $H_2S$.

Fifth, using Gibbs/equilibrium reaction hypothesis, thermodynamic study was conducted on the complete process parametrizing different reactant ratios $CH_4/H_2S$ (about 10:1, 1:1, 1:5, 1:10, 1:20, or 1:30), reactor feed temperature (about 25, 125, 225, 325, 425, 525, 625, 725, 825, 925, 1025, 1125, 1225, 1325, 1425, or 1525° C.) and feed pressure (1, 5, 9, 13, 17, 21, 25, 29 bar).

The findings of the thermodynamic study are listed below. The low-pressure operation is favorable for methane conversion using sulfur as source of radical. Slightly positive pressure (about 1-3) bar is recommended. Reaction-A is endothermic (similar to steam reforming). The higher is the temperature; the better is reaction conversion (see FIG. 5).

Figure 5:
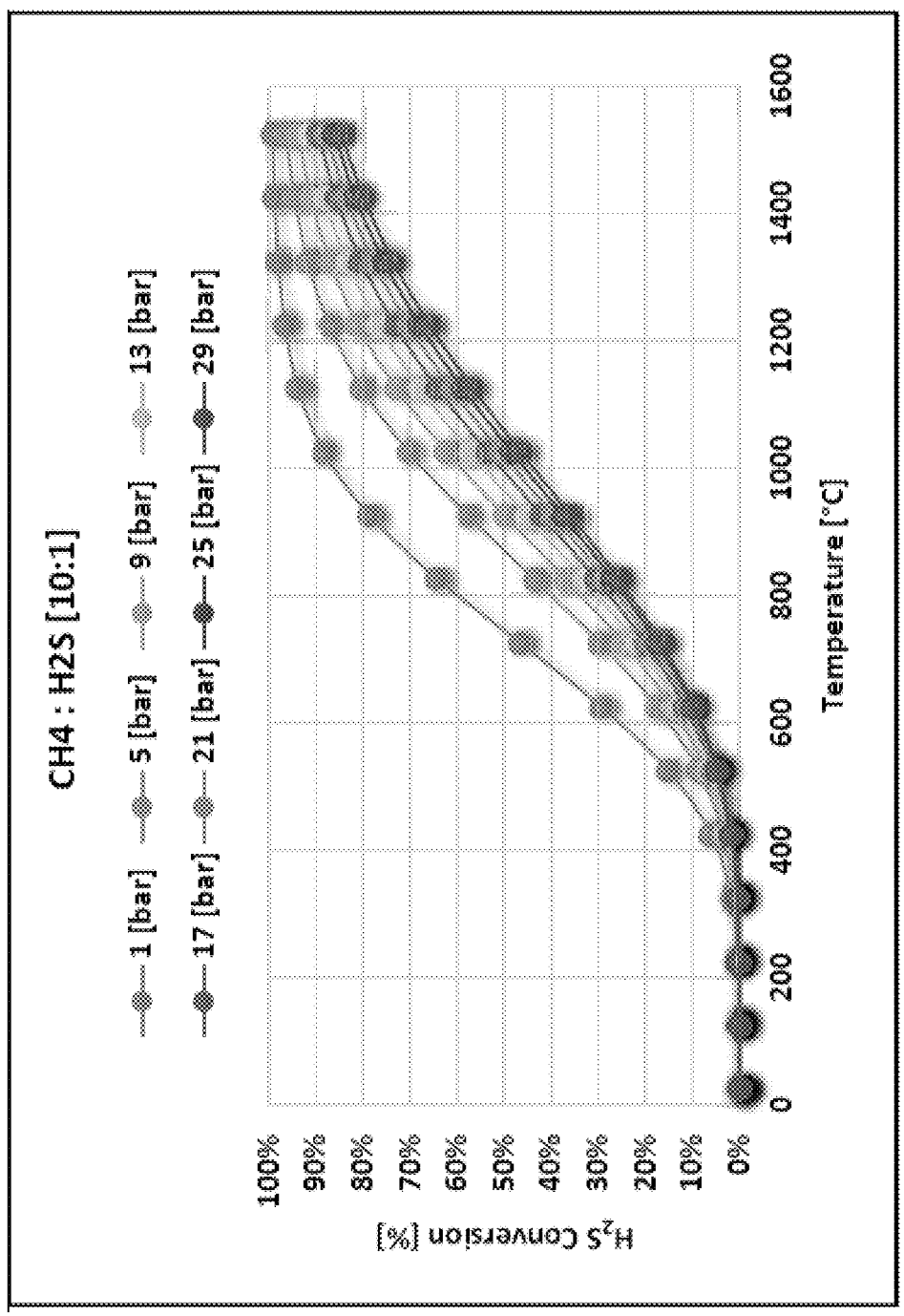
FIG. 5 illustrates an example Reactor A: $H_2S$ conversion, according to an aspect of the present disclosure.

The $H_2S$ conversion in Reactor A is illustrated in FIG. 5. Adding liquid sulfur will ensure complete sulfur conversion and reduce the heating requirements as the sulfur-methane reaction is exothermic. Increasing the methane to $H_2S$ ratio (up to 10:1, 20:1 and 30:1) would increase reaction conversion, boost desired products yield, and reduce undesired by-products. Increasing $CH_3SH$ synthesis reaction temperature up to 500° C. instead of 250° C. will boost $CS_2$ conversion from 86% to 99%.

Six, Machine Learning (ML) models were developed to derive an analytical approximation of the nonlinear relationship between the complete set of inputs and the observed simulated outputs of the methane-upgrading (MU) process. These functions are used to accurately extrapolate the performance of the MU system for any given combination of the input control parameters at a much lower computational cost compared to process simulation tools. Higher-order Multivariate Polynomial regression models (HMP) are used to fit the variation of each single dependent variable of the system, given the variability of all the independent inputs. The selection of the nth order of the polynomial model for each dependent variable is set though 10-fold cross-validated minimization of the overall Root Mean Square Error (rRMSE) of the regression residuals relative to the average of the observed output. Given ranges of $CH_4$—$H_2S$ feed-ratio (FR) between 0.4248 and 21.2203, pressure (P) between 1.0 and 29.0 bar, and temperature (T) between 25.0 and 1530.0° C. as input of the MU system, the below equations are retrieved for each output through least square unbiased estimation of the polynomial regression coefficients (terms with null coefficients are omitted):

i. $H_2S$ conversion (%)=1.406e-03+1.197e-07(FR)+4.060e-09(P)+3.814e-09(T)+1.287e-09($FR^2$)+−1.361e-09(FR×P)+1.625e-09(FR×T)+5.861e-09($P^2$)+2.340e-07(P×T)+−9.602e-08($T^2$)+−4.525e-10($FR^3$)+−4.595e-09($FR^2$×P)+1.706e-09($FR^2$×T)+−2.948e-08(FR×$P^2$)+6.235e-08(FR×P×T)+−3.918e-08(FR×$T^2$)+3.746e-10($P^3$)+1.879e-06($P^2$×T)+−2.755e-08(P×$T^2$)+2.991e-10($T^3$)+−9.691e-10($FR^4$)+−1.021e-08($FR^3$×P)+2.671e-09($FR^3$×T)+−7.977e-08($FR^2$×$P^2$)+−5.131e-08($FR^2$×P×T)+−1.326e-08($FR^2$×$T^2$)×−4.194e-07(FR×$P^3$)+6.309e-07(FR×$P^2$×T)+−1.023e-08(FR×P×$T^2$)+1.452e-10(FR×$T^3$)+−4.575e-07($P^4$)+−2.229e-07($P^3$×T)+3.900e-09($P^2$×$T^2$)+−4.495e-11(P×$T^3$)+4.237e-13($T^4$)+−1.871e-09($FR^5$)+−1.985e-08($FR^4$×P)+4.793e-09($FR^4$×T)+−1.605e-07($FR^3$×$P^2$)+−1.686e-07($FR^3$×P×T)+8.922e-10($FR^3$×$T^2$)+−9.688e-07($FR^2$×$P^3$)+−5.441e-08($FR^2$×$P^2$×T)+−1.475e-09($FR^2$×P×$T^2$)+9.447e-11($FR^2$×$T^3$)+8.681e-08(FR×$P^4$)+−1.345e-08(FR×$P^3$×T)+7.137e-11(FR×$P^2$×$T^2$)+6.909e-12(FR×P×$T^3$)+−2.523e-13(FR×$T^4$)+4.311e-08($P^5$)+5.810e-09($P^4$×T)+2.325e-11($P^3$×$T^2$)+−3.740e-12($P^2$×$T^3$)+7.403e-14(P×$T^4$)+−6.590e-16($T^5$)+6.649e-11($FR^6$)+1.548e-09($FR^5$×P)+−2.311e-10($FR^5$×T)+7.883e-09($FR^6$×$P^2$)+7.918e-09($FR^6$×P×T)+−1.221e-11($FR^4$×$T^2$)+4.455e-08($FR^3$×$P^3$)+1.688e-09($FR^3$×$P^2$×T)+7.907e-11($FR^3$×P×$T^2$)+−4.276e-12($FR^3$×$T^3$)+−3.539e-09($FR^2$×$P^4$)+4.557e-10($FR^2$×$P^3$×T)+−8.564e-12($FR^2$×$P^2$×$T^2$)+−1.548e-14($FR^2$×P×$T^3$)+1.997e-15($FR^2$×$T^4$)+4.463e-10(FR×$P^5$)+−3.678e-11(FR×$P^4$×T)+3.909e-12(FR×$P^3$×$T^2$)+−4.866e-14(FR×$P^2$×$T^3$)+−1.238e-15(FR×P×$T^4$)+5.372e-17(FR×$T^5$)+−9.509e-10($P^6$)+−3.708e-11($P^5$×T)+−1.239e-12($P^4$×$T^2$)+1.710e-14($P^3$×$T^3$)+9.359e-16($P^2$×$T^4$)+−2.585e-17(P×$T^5$)+2.265e-19($T^6$)

ii. $CS_2$ conversion (%)=−3.886e-01+2.230e-03(FR)+2.263e-02(P)+3.510e-03(T)+5.149e-03($FR^2$)+−1.299e-03(FR×P)+1.887e-05(FR×T)+−1.329e-03($P^2$)+1.099e-05(P×T)+−3.210e-06($T^2$)+−2.435e-04($FR^3$)+3.993e-05($FR^2$×P)+−6.668e-07($FR^2$×T)+1.656e-05(FR×$P^2$)+−3.505e-07(FR×P×T)+2.679e-09(FR×$T^2$)+2.425e-05($P^3$)+−2.602e-07($P^2$×T)+1.281e-09(P×$T^2$)+8.725e-10($T^3$)

iii. Benzene production rate (kgmol/h)=1.101e-03+5.171e-06(FR)+2.344e-05(P)+1.432e-06(T)+2.762e-05($FR^2$)+−2.177e-05(FR×P)+−2.936e-07(FR×T)+1.836e-04($P^2$)+7.597e-07(P×T)+−4.255e-07($T^2$)+6.027e-05($FR^3$)+−7.588e-05($FR^2$×P)+−2.025e-06($FR^2$×T)+7.786e-05(FR×$P^2$)+−4.587e-07(FR×P×T)+−1.040e-07(FR×$T^2$)+−2.836e-05($P^3$)+1.240e-06($P^2$×T)+−5.210e-08(P×$T^2$)+2.075e-09($T^3$)+1.169e-04($FR^4$)+−1.577e-04($FR^3$×P)+−4.443e-06($FR^3$×T)+3.214e-05($FR^2$×$P^2$)+−1.669e-06($FR^2$×P×T)+1.022e-07($FR^2$×$T^2$)+−4.950e-06(FR×$P^3$)+1.641e-07(FR×$P^2$×T)+−2.131e-09(FR×P×$T^2$)+−1.437e-11(FR×$T^3$)+1.014e-06($P^4$)+−2.113e-08($P^3$×T)+−3.603e-10($P^2$×$T^2$)+4.300e-11(P×$T^3$)+−1.584e-12($T^4$)+−5.645e-06($FR^5$)+7.594e-06($FR^4$×P)+2.138e-07($FR^4$×T)+−1.645e-06($FR^3$×$P^2$)+7.877e-08($FR^3$×P×T)+−4.560e-09($FR^2$×$T^2$)+1.869e-07($FR^2$×$P^3$)+−6.875e-09($FR^2$×$P^2$×T)+1.082e-10($FR^2$×P×$T^2$)+−1.197e-13($FR^2$×$T^3$)+1.457e-08(FR×$P^4$)+−2.898e-10(FR×$P^3$×T)+1.264e-12(FR×$P^2$×$T^2$) +−5.860e-14(FR×P×$T^3$)+3.064e-15(FR×$T^4$)+−8.657e-09($P^5$)+−4.065e-10($P^4$×T) +3.192e-11($P^3$×$T^2$)+−6.417e-13($P^2$×$T^2$)+−3.624e-15(P×$T^4$)+3.615e-16($T^5$)

iv. Toluene production rate (kgmol/h)=7.066e-04+3.366e-06(FR)+1.529e-05(P) +1.105e-06(T)+1.799e-05($FR^2$)+−1.422e-05(FR×P)+−1.242e-07(FR×T)+1.198e-04(P)+4.772e-07(P×T)+−2.772e-07($T^2$)+3.925e-05($FR^3$)+−4.955e-05($FR^2$×P)+−1.303e-06($FR^2$×T)+5.078e-05(FR×$P^2$)+−3.034e-07(FR×P×T)+−6.778e-08(FR×$T^2$)+−1.850e-05($P^3$)+8.071e-07($P^2$×T)+−3.384e-08(P×$T^2$)+1.350e-09($T^3$)+7.612e-05($FR^4$)+−1.030e-04($FR^3$×P)+−2.912e-06($FR^3$×T)+2.093e-05($FR^2$×$P^2$)+−1.084e-06($FR^2$×P×T)+6.654e-08($FR^2$×$T^2$)+−3.223e-06(FR×$P^3$)+1.067e-07(FR×$P^2$×T)+−1.385e-09(FR×P×$T^2$)+−9.378e-12(FR×$T^3$)+6.617e-07($P^4$)+−1.378e-08($P^3$×T)+−2.344e-10($P^2$×$T^2$)+2.792e-11(P×$T^3$)+−1.030e-12($T^4$)+−3.676e-06($FR^5$)+4.959e-06($FR^4$×P)+1.400e-07($FR^4$×T)+−1.072e-06($FR^3$×$P^2$)+5.115e-08($FR^3$×P×T)+−2.969e-09($FR^3$×$T^2$)+1.218e-07($FR^2$×$P^3$)+−4.470e-09($FR^2$×$P^2$×T)+7.030e-11($FR^2$×P×$T^2$)+−7.598e-14($FR^2$×$T^3$)+9.425e-09(FR×$P^4$)+−1.880e-10(FR×$P^3$×T)+8.192e-13(FR×$P^2$×$T^2$) +−3.784e-14(FR×P×$T^3$)+1.990e-15(FR×$T^4$)+−5.660e-09($P^5$)+−2.638e-10($P^4$×T) +2.076e-11($P^3$×$T^2$)+−4.173e-13($P^2$×$T^3$)+−2.345e-15(P×$T^4$)+2.351e-16($T^5$)

v. P-xylene production rate (kgmol/h)=1.187e-04+5.798e-07(FR)+2.584e-06(P)+2.623e-07(T)+3.099e-06($FR^2$)+−2.396e-06(FR×P)+5.571e-09(FR×T)+2.028e-05($P^2$)+7.561e-08(P×T)+−4.766e-08($T^2$)+6.762e-06($FR^3$)+−8.355e-06($FR^2$×P)+−2.207e-07($FR^2$×T)+8.604e-06(FR×$P^2$)+−5.366e-08(FR×P×T)+−1.165e-08(FR×$T^2$)+−3.135e-06($P^3$)+1.390e-07($P^2$×T)+−5.791e-09(P×$T^2$)+2.314e-10($T^3$)+1.312e-05($FR^4$)+−1.737e-05($FR^3$×P)+−5.144e-07($FR^3$×T)+3.561e-06($FR^2$×$P^2$)+−1.846e-07($FR^2$×P×T)+1.144e-08($FR^2$×$T^2$)+−5.486e-07(FR×$P^3$)+1.837e-08(FR×$P^2$×T)+−2.398e-10(FR×P×$T^2$)+−1.630e-12(FR×$T^3$)+1.119e-07($P^4$)+−2.403e-09($P^3$×T)+−4.026e-11($P^2$×$T^2$)+4.780e-12(P×$T^3$)+−1.764e-13($T^4$)+−6.334e-07($FR^5$)+8.363e-07($FR^4$×P)+2.471e-08($FR^4$×T)+−

$1.823e\text{-}07(FR^3\times P^2)+8.717e\text{-}09(FR^3\times P\times T)+-5.105e\text{-}10(FR^3\times T^2)+2.076e\text{-}08(FR^2\times P^3)+-7.689e\text{-}10(FR^2\times P^2\times T)+1.213e\text{-}11(FR^3\times P\times T^2)+-1.296e\text{-}14(FR^2\times T^3)+1.598e\text{-}09(FR\times P^4)+-3.263e\text{-}11(FR\times P^3\times T)+1.402e\text{-}13(FR\times P^2\times T^2)+-6.217e\text{-}15(FR\times P\times T^3)+3.467e\text{-}16(FR\times T^4)+-9.475e\text{-}10(P^5)+-4.472e\text{-}11(P^4\times T)+3.570e\text{-}12(P^3\times T^2)+-7.170e\text{-}14(P^2\times T^3)+-3.987e\text{-}16(P\times T^4)+4.023e\text{-}17(T^5)$ vi. Naphthalene production rate (kgmol/h)=$-1.329e\text{-}03+5.520e\text{-}05(FR)+3.064e\text{-}04(P)+-2.057e\text{-}05(T)+1.394e\text{-}04(FR^2)+2.225e\text{-}05(FR\times P)+-7.163e\text{-}06(FR\times T)+3.755e\text{-}05(P^2)+-2.560e\text{-}06(P\times T)+5.370e\text{-}08(T^2)+2.775e\text{-}04(FR^3)+-1.950e\text{-}04(FR^2\times P)+-8.821e\text{-}10(FR^2\times T)+2.577e\text{-}05(FR\times P^2)+-9.720e\text{-}07(FR\times P\times T)+3.682e\text{-}08(FR\times T^2)+-3.272e\text{-}06(P^3)+1.692e\text{-}07(P^2\times T)+-3.784e\text{-}09(P\times T^2)+1.522e\text{-}10(T^3)+-1.338e\text{-}05(FR^4)+9.040e\text{-}06(FR^3\times P)+1.733e\text{-}08(FR^3\times T)+-1.053e\text{-}06(FR^2\times P^2)+4.301e\text{-}08(FR^2\times P\times T)+-1.714e\text{-}09(FR^2\times T^2)+-5.663e\text{-}08(FR\times P^3)+-9.790e\text{-}11(FR\times P^2\times T)+5.473e\text{-}11(FR\times P\times T^2)+-1.672e\text{-}12(FR\times T^3)+3.558e\text{-}08(P^4)+6.583e\text{-}10(P^3\times T)+-1.078e\text{-}10(P^2\times T^2)+3.027e\text{-}12(P\times T^3)+-8.091e\text{-}14(T^4)$ vii. Side product $CH_4$ production rate (kgmol/h)=$8.478e+00+2.386e+01(FR)+4.028e\text{-}02(P)+-6.792e\text{-}04(T)+-9.204e\text{-}01(FR^2)+-1.118e\text{-}03(FR\times P)+5.282e\text{-}05(FR\times T)+-1.494e\text{-}03(P^2)+4.540e\text{-}05(P\times T)+-1.223e\text{-}06(T^2)$ viii. Undesired $H_2S$ production rate (kgmol/h)=$4.356e+01+-3.115e\text{-}01(FR)+5.729e\text{-}02(P)+4.966e\text{-}04(T)+-7.867e\text{-}01(FR^2)+1.812e\text{-}02(FR\times P)+1.307e\text{-}04(FR\times T)+-1.525e\text{-}02(P^2)+2.208e\text{-}04(P\times T)+-2.126e\text{-}06(T^2)+-1.566e+00(FR^3)+-4.218e\text{-}03(FR^2\times P)+-9.777e\text{-}05(FR^2\times T)+-1.293e\text{-}04(FR\times P^2)+7.762e\text{-}06(FR\times P\times T)+-3.539e\text{-}07(FR\times T^2)+9.264e\text{-}04(P^3)+-2.253e\text{-}05(P^2\times T)+2.787e\text{-}07(P\times T^2)+-3.227e\text{-}09(T^3)+7.539e\text{-}02(FR^4)+1.535e\text{-}04(FR^3\times P)+4.307e\text{-}06(FR^3\times T)+2.567e\text{-}05(FR^2\times P^2)+-6.676e\text{-}07(FR^2\times P\times T)+1.740e\text{-}08(FR^2\times T^2)+-1.321e\text{-}05(FR\times P^3)+4.184e\text{-}07(FR\times P^2\times T)+-7.104e\text{-}09(FR\times P\times T^2)+9.004e\text{-}11(FR\times T^2)+-1.581e\text{-}05(P^4)+4.460e\text{-}07(P^3\times T)+-4.511e\text{-}09(P^2\times T^2)+-7.440e\text{-}12(P\times T^3)+9.724e\text{-}13(T^4)$ Techno-Economics The energy prices are based on the price in Qatar. The parameters used for the analysis are shown in Table 5. The cost analysis is shown in Table 6. The prices are based on February-2020 market figures. The cost of catalysts are not included. The ArC10 cost is not included.

TABLE 5

Calculation parameters

| Item | Unit | Price |
|---|---|---|
| Electricity | $/kWh | 0.05 |
| hr-operation | hrs/year | 8760 |
| Fuel Gas | $/MMBTU | 1.65 |
| Sulfur | $/Ton | 80 |
| Methane | $/MMBTU | 4.31 |
| BTX | $/Ton | 709 |

TABLE 6

Cost Analysis

| Group | Item | Value | Unit | Cost [$/year] |
|---|---|---|---|---|
| Reactions | Feed Heater, Duty | 2.22 | MMBTU/hr | 31991 |
| | Methane Feedstock, Flow | 61 | kg/hr | 9815 |
| | Sulphur Feedstock, Flow | 289 | kg/hr | 202531 |
| Propane Cycle | Pre-Cooler (Air-Cooler), Duty | 314.70 | KWth | 2606 |
| | Compressor, Duty | 138.6 | KW | 60044 |
| | Air-Cooled Condenser, Duty | 273.36 | KWth | 2264 |
| AGR | Reboiler "Steam", Duty | 0.51 | MMBTU/hr | 7403 |
| | Air Coolers Amine, Duty | 0.42 | KWth | 3 |
| | Air Coolers H2S condenser, Duty | 81.30 | KWth | 673 |
| | Circulation Amine Pump, Duty | 0.2 | KW | 87 |
| | Water Reflux Pump, Duty | 0.0027 | KW | 1 |
| | Amine Makeup | | | 445 |
| | Corrosion & Maintenance | | | 1661 |
| Product | BTX, Flow | 159.60 | kg/hr | 990780 |
| | Unit Production COST | | $/Ton | 229 |
| | Unit Profit | | $/Ton | 480 |

TABLE 7

Cost share breakdown

| Section | Item | Overall Share | | Section Share |
|---|---|---|---|---|
| Reactions | Feed Heater | 10.01% | 76.47% | 13.09% |
| | Methane Feedstock | 3.07% | | 4.02% |
| | Sulfur Feedstock | 63.39% | | 82.89% |
| Propane Cycle | Pre-Cooler (Air-Cooler) | 0.82% | 20.32% | 4.01% |
| | Compressor | 18.79% | | 92.50% |
| | Air-Cooled Condenser | 0.71% | | 3.49% |
| AGR | Reboiler "Steam" | 2.32% | 3.21% | 72.06% |
| | Air Coolers Amine | 0.00% | | 0.03% |
| | Air Coolers $H_2S$ condenser | 0.21% | | 6.55% |
| | Circulation Amine Pump | 0.03% | | 0.84% |
| | Water Reflux Pump | 0.00% | | 0.01% |
| | Amine Makeup | 0.14% | | 4.33% |
| | Corrosion & Maintenance | 0.52% | | 16.17% |

Figure 6:
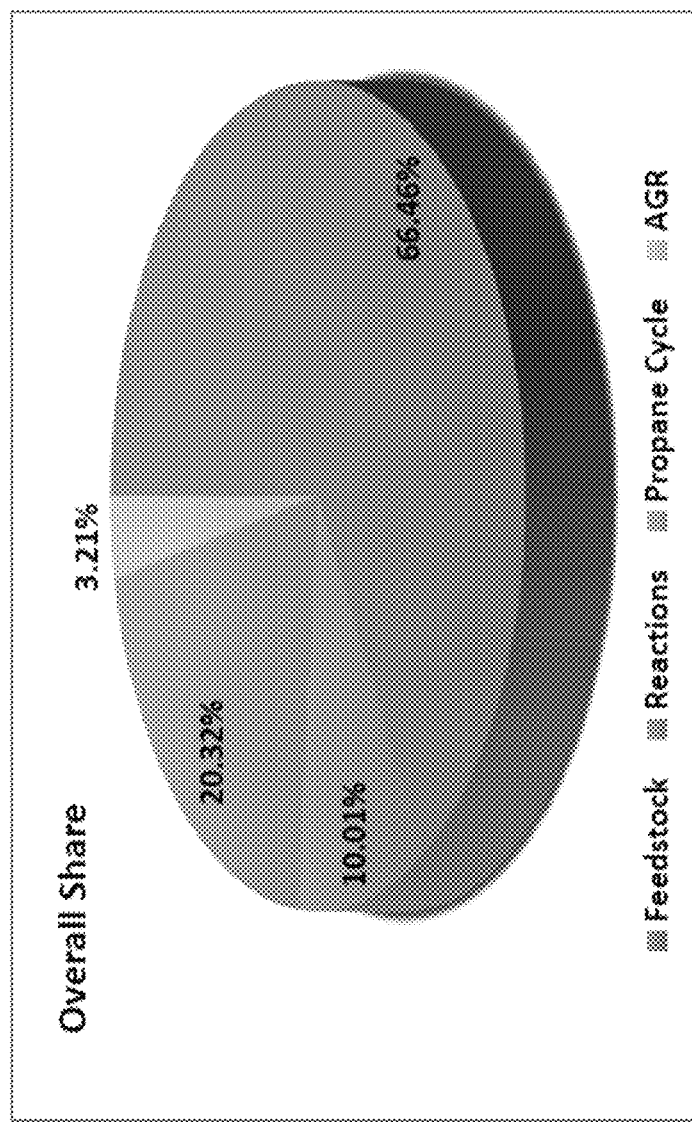
FIG. 6 illustrates an example breakdown cost share for the methane upgrading process, according to an aspect of the present disclosure.
Figure 7:
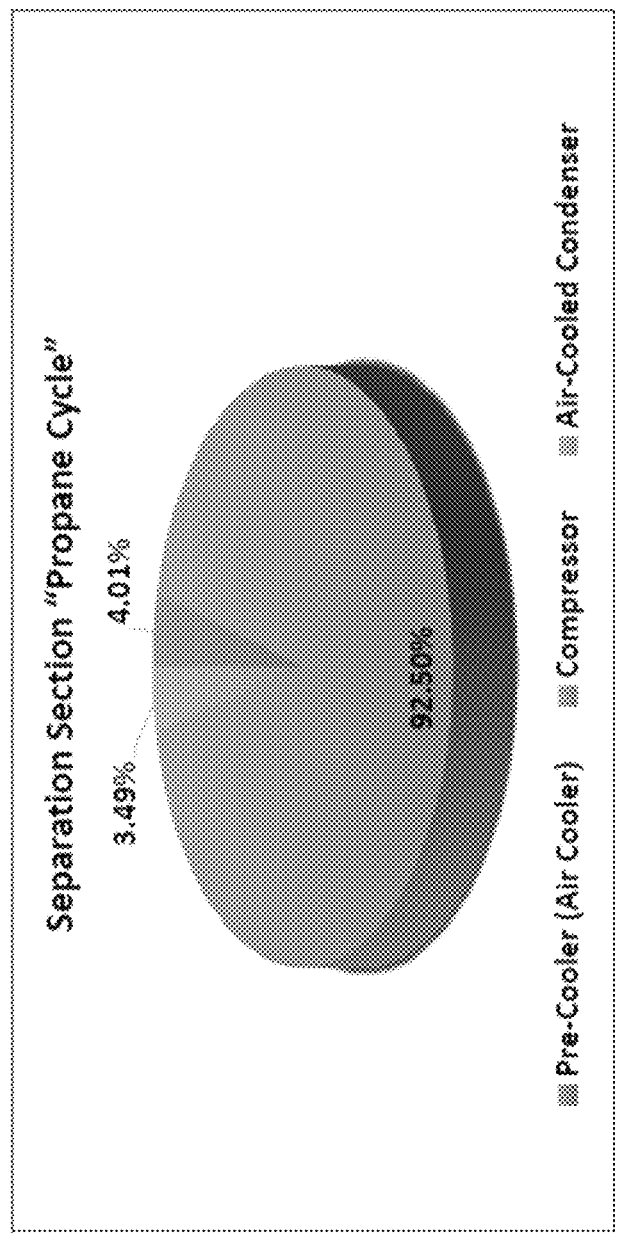
FIG. 7 illustrates an example breakdown cost share for Propane cycle, according to an aspect of the present disclosure.
Figure 8:
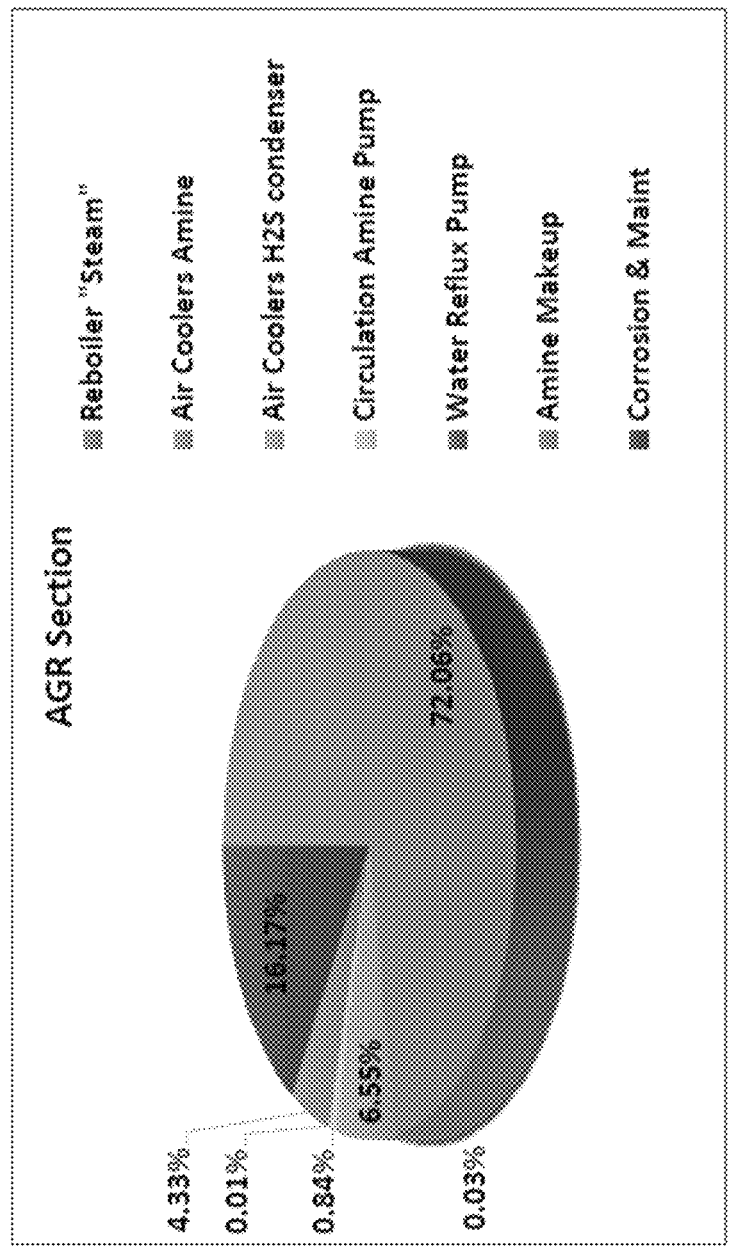
FIG. 8 illustrates an example breakdown cost share for AGR section, according to an aspect of the present disclosure.
Figure 9:
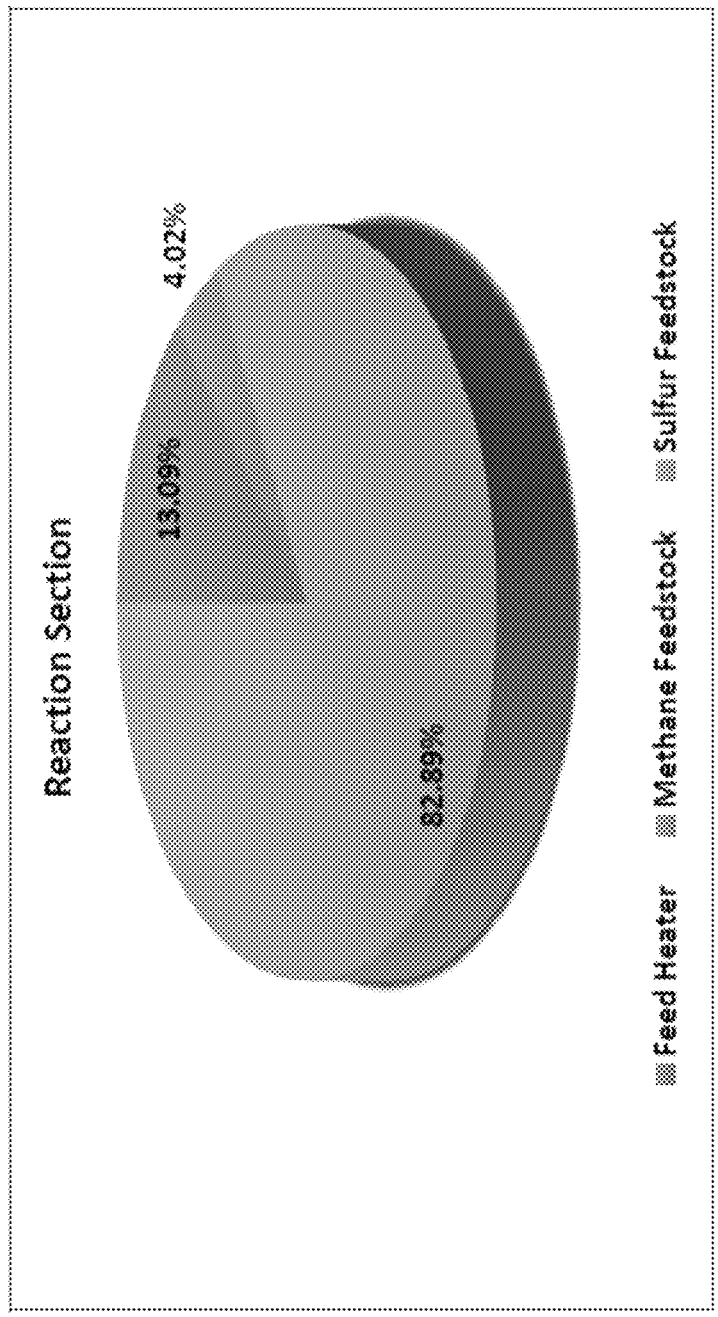
FIG. 9 illustrates an example breakdown cost share for Reaction section, according to an aspect of the present disclosure.

The breakdown cost share for the methane upgrading process is shown in FIG. 6. The breakdown cost share for Propane cycle is shown in FIG. 7. The breakdown cost share for AGR section is described in FIG. 8. The breakdown cost share for Reaction section is described in FIG. 9.

Figure 10:
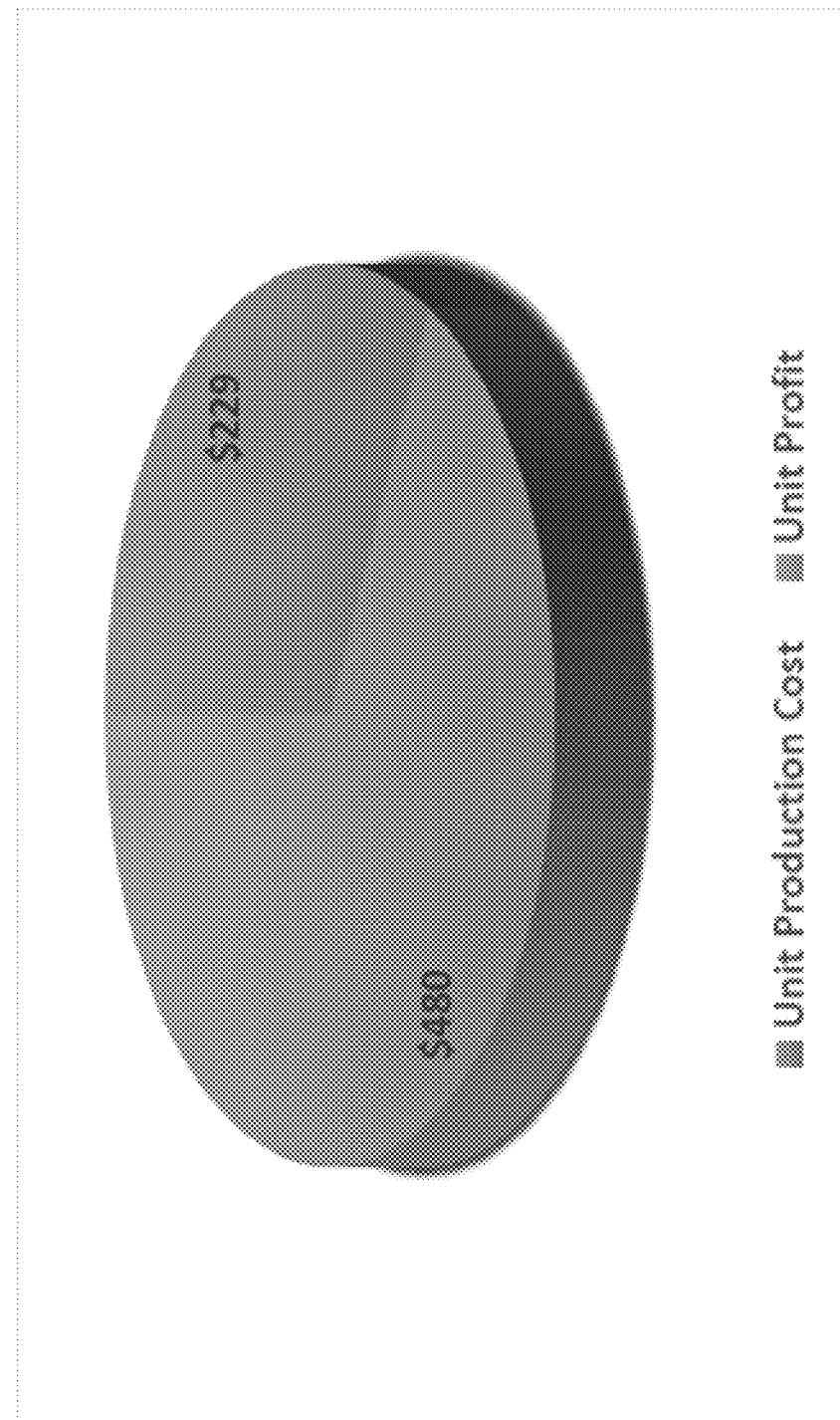
FIG. 10 illustrates an example preliminary techno-economics summary, according to an aspect of the present disclosure.

The preliminary Techno-economic analysis shows a viable process for BTX production. The preliminary Techno-economics summary is described in FIG. 10.

Figure 11:
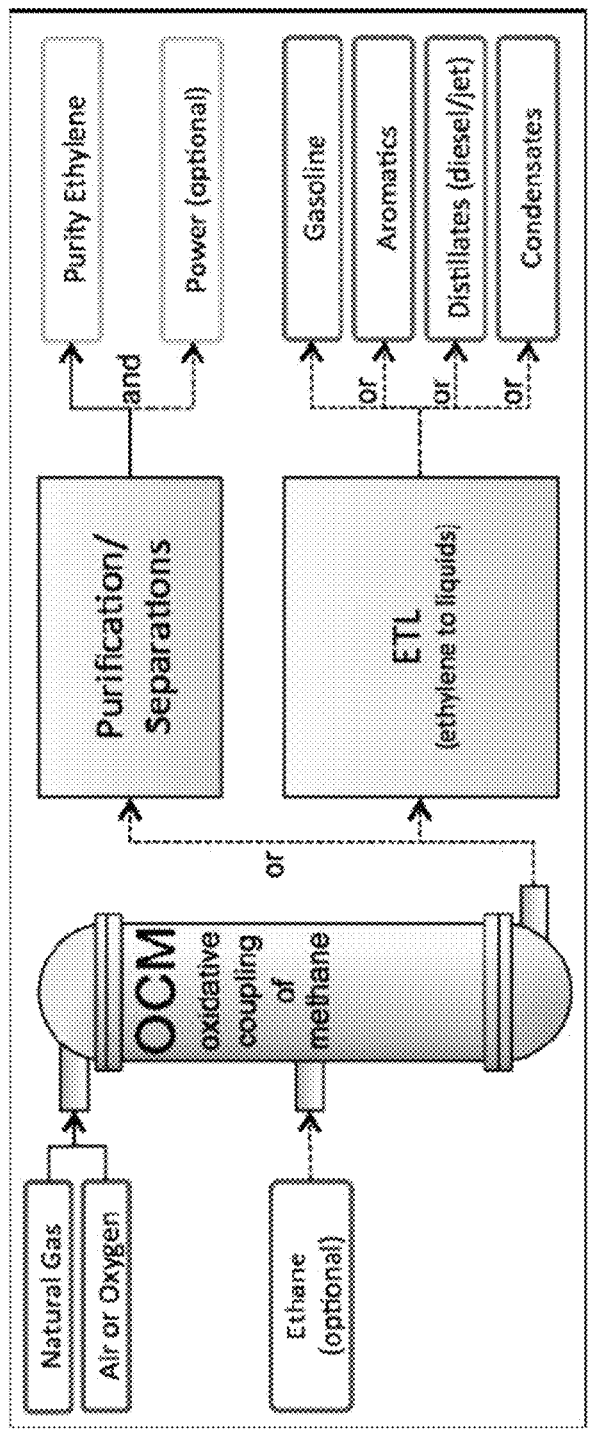
FIG. 11 illustrates an example OCM Schematic block diagram, according to an aspect of the present disclosure.

There are many techniques to produce olefins and aromatics (benzene, toluene and xylene). Most of which have methane as feedstock or through Fischer-Tropsch (FT) process. The latest technology for methane conversion to olefins and aromatics is called Oxidative coupling of methane (OCM, see FIG. 11). The OCM Schematic block diagram is described in FIG. 11.

The OCM process targets to produce olefins and aromatics by combustion of methane with pure oxygen or air. This process suffers from multiple operational and scale up issues, including: Low reaction conversion (<10%); Low selectivity to desired products and high yield for side and by-products; Highly exothermic reaction; Potential explosion hazards; Formation of Hot spots; Catalyst deactivation; Utilization of pure oxygen, which is expensive and requires an air-separation plant; and Separation techniques are expensive and complicated.

Moreover, Qatar has the opportunity to increase the benefit of its natural gas reserves, in addition to liquefaction and exportation as LNG or burning it for power generation.

On top of that, $H_2S$ is always accompanied with raw natural gas extracted from gas/oil wells, which require treatments using acid gas removal plants followed by Claus process for sulfur recovery.

Reserves of natural gas and oil in Qatar are among the largest ones in the world, with the Oil and Gas sector constituting the backbone of the country's economy.

In the field of oil and gas, sulphur represents the Achilles heel for fuel production and plants maintenance. Natural gas and oil contain $H_2S$ and a wide variety of organic sulphur-based compounds (Such as Methyl Mercaptan $CH_3SH$). These must be removed before the natural gas can be used as a feedstock for the chemical industry because of their poisonous effect. Equally, they have to be removed if natural gas or oil are to be used as fuels. Otherwise, large amounts of sulphur dioxide, a very dangerous pollutant, will be released into the atmosphere when the fuels are burnt. Additionally, $H_2S$ is one of the main causes of costly corrosion in refinery plants. Qatar is also home to one of the world's largest sulphur processing plants, in the Ras Laffan industrial zone, which converts sulphur from the giant North Field gas field into fertilizer and other valuable products.

In this scenario, despite the remarkable number of academic and industrial entities in the country, involved in the field of oil and gas, applied research including sulphur-containing compounds is extremely limited because of the high toxicity of such chemicals. In addressing the challenge, Qatar Foundation would have the opportunity to be the leading edge in this field, and contribute significantly to Qatar's economy, the whole Gulf region, and the world.

The present disclosure focuses on a new "Non-oxygen type of oxidizers" process for methane upgrading to produce products that are more valuable as well as removing the toxic impurity (sulphur compounds) by utilizing the Sulphur as a source of radical. The global aim is to convert the Methyl-Mercaptan to much more valuable aromatics and olefins.

This technology of the present disclosure has multiple benefits including the following. This technology creates values for the country's economy, as the expected unit profit out from this technology is $480/Ton-BTX compared to $50/Ton-methane (pipeline export rate for methane). The methane value could be upgraded ten-folds by using this technology. The removal of $H_2S$ and other sulfur poisonous compounds through a low-cost conversion process rather than removing the sulfur and disposing is cost effective. This technology tackles the existing problems in the current OCM technologies. Using the present technology protects the environment from flaring compounds such as SO2.

The present disclosure provides, for example: 1) Completing the process flow diagram for the conversion, integration and separation process (See FIG. 1); 2) Using process simulation tools (Aspen Engineering and ProMax) for simulating this technology to calculate the process streams balance, utility consumption and equipment performance at design conditions; 3) Calculating the system mass and heat balance (See Table. 1); 4) Conducting techno-economic analyses to determine the system overall performance and competitiveness compared to technologies currently available in the market. (See Table 5-7 and FIGS. 6-10); 5) Conducting thermodynamic parametric analysis on different feed ratios, reaction conditions (Pressure & Temperature) to derive the optimum operating conditions. (see FIG. 5); 6) Utilizing machine learning models to reproduce the effect of each control parameter (Feed ratio, Pressure and Temperature) on the main output parameters ($H_2S$ conversion, $CS_2$ conversion, BTX production rate, side product $CH_4$ rate and undesired $H_2S$ rate), for any combination of inputs; and 7) Using variance-based sensitivity analysis techniques in combination with the learning models to determine the simultaneous multi-input/multi-output relationship between the different parameters of the MU system and assessing how much each single input contributes to each other outputs in terms of their variance (first-order), or how the paired interactions of the inputs influences the different outputs (second-order).

Data

Figure 12:
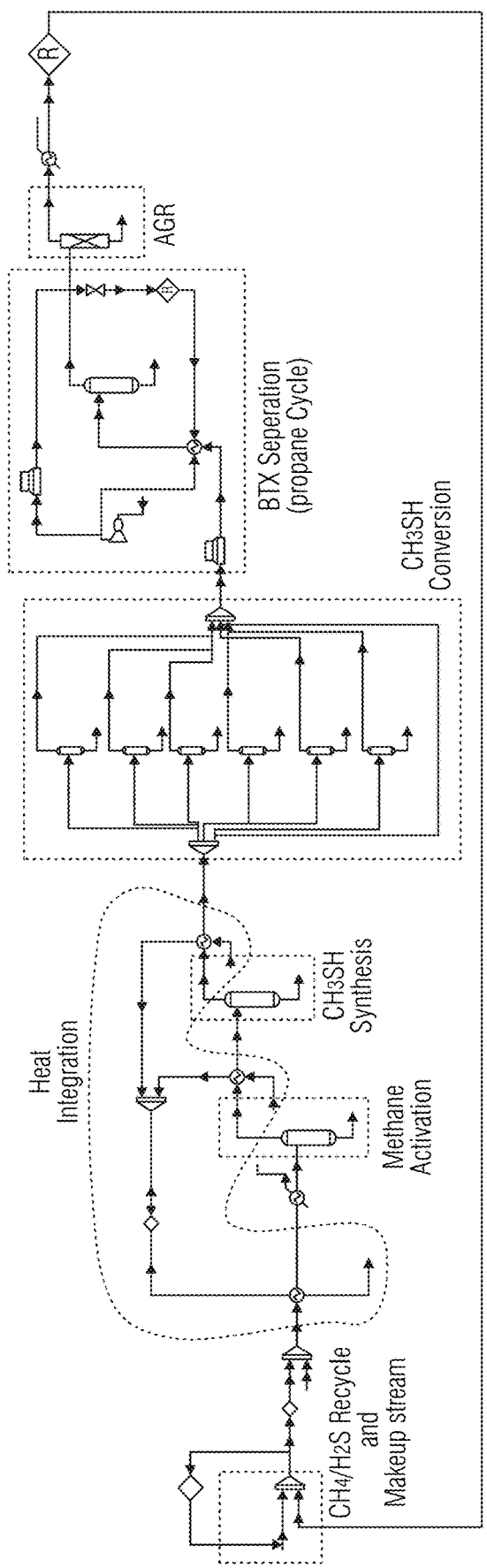
FIG. 12 illustrates an example process simulation for methane upgrading technology, according to an aspect of the present disclosure.

The available data set consists of a total of 384 simulated observations of the 8 outputs under study ($H_2S$ Conv. %, $CS_2$ Conv. %, Naphthalene, p-Xylene, Toluene, Benzene, $H_2S$, and Methane) given the variation of 3 input variables (feed-ratio, pressure, and temperature). Table 8 summarizes the descriptive statistics of the inputs and outputs used for this study. The process simulation for methane upgrading technology is described in FIG. 12.

Methodology

A regression fit is first performed to accurately approximate the nonlinear multivariable relationship between the three independent variables (inputs) and each dependent variable (output). Higher-order Multivariate Polynomial regression models (HMP) have been used to minimize the residual sum of squares between the simulated observations and the targets predicted by the learning function (see eq. 1, with n as the power order and i to identify the specific input). The selection of the Nth degree is performed through 10-fold cross-validation minimization of the relative Root Mean Square Error (rRMSE, see eq. 2) to both reduce the likelihood of overfitting and to maximize the generalization of the final solution.

Following is the mathematical expression of the HMP model that fits the functional relationship between the set of inputs ($x_i$, $x_2$, $x_3$, i.e.: feed-ration, pressure and temperature) and each single output:

$$\text{Output} = HMP_n(x_1, x_2, x_3) = \beta_0 + \sum_{i_1, i_2, i_3 < n} \beta_{i_1, i_2, i_3} x_1^{i_1} x_2^{i_2} x_3^{i_3} + \varepsilon \quad (1)$$

With $\beta_{i1,2,i3}$ the polynomial regression coefficients and $\varepsilon$ the residual error.

Below is instead the mathematical expression of the performance measure used to select the nth degree order of the HMPn model for each output, the relative Root Mean Square Error (rRMSE), where for relative it is considered its normalization to the variable mean value.

$$rRMSE = \frac{\sqrt{\frac{\sum_{i=1}^{N}(\text{output}_{obs_i} - \text{output}_{est_i})^2}{N}}}{\text{average}(\text{output}_{obs})} \quad (2)$$

With N, as the number of observations, $\text{output}_{obs}$ the observed values of the output and $\text{output}_{est}$ the output result estimated by the model.

If the cross-validated rRMSE results higher than 3% for any of the output function, more advanced machine learning models such as gradient boosted regression trees, are tested as alternative regression model tools to run the consecutive sensitivity analysis.

TABLE 8

Data set descriptive statistics

| | Inputs | | | Outputs | | | | | | | |
|---|---|---|---|---|---|---|---|---|---|---|---|
| | Feed Ratio kgmol/h | Preassure bar | Temp. °C. | $H_2S$ Conv. % | $CS_2$ Conv. % | Naphthalene kgmol/h | p-Xylene kgmol/h | Toluene kgmol/h | Benzene kgmol/h | $H_2S$ kgmol/h | Methane kgmol/h |
| count | 384 | 384 | 384 | 384 | 384 | 384 | 384 | 384 | 384 | 384 | 384 |
| mean | 7.92 | 15.0 | 775.09 | 0.20 | 0.76 | 0.07 | 0.02 | 0.14 | 0.22 | 23.28 | 57.19 |
| std dev | 9.44 | 9.18 | 461.73 | 0.26 | 0.38 | 0.07 | 0.03 | 0.16 | 0.25 | 15.55 | 33.66 |
| min | 0.42 | 1.0 | 25.0 | 0.0 | 0.0 | 0.0 | 0.0 | 0.0 | 0.0 | 2.65 | 13.31 |
| 25%* | 0.42 | 8.0 | 400.0 | 0.0 | 0.69 | 0.00 | 0.00 | 0.00 | 0.01 | 4.68 | 18.34 |
| 50%* | 2.12 | 15.0 | 755 | 0.08 | 0.98 | 0.04 | 0.02 | 0.09 | 0.14 | 25.03 | 54.63 |
| 75%* | 21.22 | 22.2 | 1150 | 0.27 | 1.00 | 0.11 | 0.04 | 0.23 | 0.36 | 40.76 | 99.39 |
| max | 21.22 | 29.0 | 1530 | 0.99 | 1.00 | 0.32 | 0.12 | 0.70 | 1.08 | 43.22 | 100.16 |

*Percentile

For the variance-based sensitivity analysis the so-called Sobol indices is used. This technique decomposes the variance of the output of the model under study into fractions, which can be attributed to the different inputs of the system. For each input of the system, this analysis tool gives the measures of sensitivity of the specific input on the final output in terms of changes in variance. The advantage in using variance-based measures of sensitivity is that they measure sensitivity across the whole input space, they can deal with non-linear responses, and they can measure the effect of interactions in non-additive systems.

The sensitivity of each input is here presented in terms of sensitivity indices:

First-order indices: measure the contribution to the output variance by each single model input alone: how much the output changes due to the changes of each specific input.

Second-order indices: measure the contribution to the output variance caused by the interaction of two model inputs: how much the output changes due to the combined-change of each specific couple of inputs (e.g. change in y due to $x_1$-$x_2$ interaction).

Total-order index: measures the contribution to the output variance caused by a model input, including both its first-order effects (the input varying alone) and all higher-order interactions.

Results

Claim number 6 reports the polynomial equation of each output of the MU system with the respective multivariate and multi-order-effect β coefficients of the trained HMP models. Following are the results of the sensitivity analysis:

TABLE 9

First-order indices

| | Feed-ratio | Feed-ratio | Pressure |
|---|---|---|---|
| $H_2S$ Conv. % | 0.71% | 21.86% | 41.27% |
| $CS_2$ Conv. % | 0.00% | 0.91% | 98.32% |
| Naphthalene | 12.79% | 21.55% | 54.55% |
| p-Xylene | 3.42% | 20.44% | 48.75% |
| Toluene | 3.13% | 20.50% | 48.98% |
| Benzene | 3.00% | 20.40% | 49.22% |
| $H_2S$ | 99.47% | 0.00% | 0.00% |
| Methane | 98.56% | 0.02% | 0.01% |

How to read the table 9: p % of the output variance is caused by the variance in input $X_1$, while the remaining q % and r % by the variance of $X_2$ and $X_3$, respectively.

How to read the table 9: p % of the output variance is caused by the variance in input $X_1$, while the remaining q % and r % by the variance of $X_2$ and $X_3$, respectively.

TABLE 10

Second-order indices

| | Feed-ratio - Pressure | Feed-ratio - Temperature | Pressure - Temperature |
|---|---|---|---|
| $H_2S$ Conv. % | 11.47% | 15.82% | 9.03% |
| $CS_2$ Conv. % | 0.18% | 0.21% | 0.32% |
| Naphthalene | 7.13% | 3.78% | 2.18% |
| p-Xylene | 12.41% | 14.58% | 3.42% |
| Toluene | 12.45% | 14.56% | 3.40% |
| Benzene | 12.39% | 14.59% | 3.41% |
| $H_2S$ | 0.02% | 0.02% | 0.00% |
| Methane | 0.15% | 0.16% | 0.00% |

How to read the table 10: $p_{ij}$ % of the output variance is caused by the interaction of $X_i$ and $X_j$.

Accuracy

The reported multi-variate polynomial approximations include the following relative errors (rRMSE):

TABLE 11 rRMSE %

| | rRMSE |
|---|---|
| $H_2S$ Conv. % | 3.56% |
| $CS_2$ Conv. % | 15.94%* |
| Naphthalene | 5.15% |
| p-Xylene | 2.39% |
| Toluene | 2.39% |
| Benzene | 2.39% |
| $H_2S$ | 0.66% |
| Methane | 0.49% |

*For $CS_2$ Conv. % gradient boosted regression trees were used for the sensitivity analysis, with a resulting rRMSE of 1.51%.

The present technology focuses on a new "Non-oxygen type of oxidizers" process for methane upgrading to produce products that are more valuable as well as removing toxic impurity (Sulphur compounds) by utilizing the Sulphur as a source of radical. The final aim is to convert the Methyl-Mercaptan to much more valuable products such as aromatics and olefins. This technology has multiple benefits including, for example:

i. Creating value for the country economy as the expected unit profit out from this technology is $480/Ton-BTX compared to $50/Ton-methane (pipeline export rate for methane). The methane value could be upgraded ten-folds through this technology.

ii. Removal of $H_2S$ and other sulfur poisonous compounds through low-cost conversion process rather than removing the sulfur and disposing it.
iii. Utilizing only 3.36% of required methane as makeup and the rest is recycled.
iv. High BTX separation (99% recovery)
v. Tackling the existing problems in the current OCM technologies.
vi. Protecting the environment from flaring compounds such as $SO_2$.
vii. Less exothermic reaction than OCM
viii. No $CO_2$ generation.
ix. A competitive alternative to the Claus process.
x. Can be designed to directly convert sour gases to olefins without pre-treatment.
xi. Simpler and effective heat management compared to FT-chemistry an OCM technology.
xii. No reaction hot spots.
xiii. Generically, products selectivity as well as separation are easier and less expensive compared to OCM.
xiv. Non-explosive reactions.

All percentages expressed herein are by weight of the total weight of the composition unless expressed otherwise. When reference herein is made to the pH, values correspond to pH measured at 25° C. with standard equipment.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y."

Where used herein, the terms "example" and "such as," particularly when followed by a listing of terms, are merely exemplary and illustrative and should not be deemed to be exclusive or comprehensive.

The term "substantially no" as used in reference to a particular component means that any of the component present constitutes less than about 2.0% by weight, such as less than about 1.0% by weight, preferably less than about 0.5% by weight or, more preferably, less than about 0.1% by weight.

Embodiments of the present disclosure are further described in Exhibit A (Novel System and Method for Low-Cost Methane Upgrading to Added-Valuable Products) which is incorporated herein by reference and submitted with the present disclosure.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way.

It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention claimed is:

1. A process for converting methane ($CH_4$) to higher hydrocarbons including olefins and aromatic hydrocarbons, the process comprising:
(i) supplying a first feedstock comprising methane, hydrogen sulfide ($H_2S$), and a first catalytic material to a first reactor;
(ii) operating the first reactor under a first reaction condition effective to convert at least a portion of the methane and hydrogen sulfide to carbon disulfide ($CS_2$) and hydrogen ($H_2$);
(iii) supplying a second feedstock comprising the resulted carbon disulfide ($CS_2$) and hydrogen ($H_2$) from step (ii) and a second catalytic material to a second reactor;
(iv) operating the second reactor under a second reaction condition effective to convert at least a portion of the carbon disulfide ($CS_2$) and hydrogen ($H_2$) to methanethiol ($CH_3SH$) and hydrogen sulfide ($H_2S$);
(v) feeding a third feedstock comprising the resulted methanethiol ($CH_3SH$) and hydrogen ($H_2$) from step (iv) and a third catalytic material to a third reactor;
(vi) operating the third reactor under a third reaction condition effective to convert at least a portion of the methanethiol ($CH_3SH$) to produce the higher hydrocarbons;
supplying the first feedstock comprising methane, hydrogen sulfide ($H_2S$), and a first catalytic material to a first economizer to be preheated to reach a temperature in a range of about 250-900° C. before supplying to the first reactor; and supplying the preheated first feedstock from the first economizer to a first reactor; and
supplying the second feedstock comprising the resulted carbon disulfide ($CS_2$) and hydrogen ($H_2$) from step (ii) and the second catalytic material to a second economizer before supplying to the second reactor; supplying water to the second economizer; conducting a heat exchange in the second economizer to reduce the temperature of the second feedback down to a range of about 250-300° C. and to recover the heat from the second feedstock to heat up the water to form a steam; and supplying the second feedstock with reduced temperature from the second economizer to the second reactor.

2. The process of claim 1, wherein the first feedstock further comprises liquid sulphur ($S_8$), and the aromatic hydrocarbons include benzene, toluene and xylene, and optionally naphthalene.

3. The process of claim 1, wherein the first catalytic material comprises a $Pt/Al_2O_3$ catalyst.

4. The process of claim 1, wherein the first reaction condition in the first reactor comprises a temperature in a range of about 800-1000° C.; a pressure of about 1-3 bar; and an outlet temperature of the first reactor in a range of about 650-750° C.

5. The process of claim 1, wherein the conversion of the methane and $H_2S$ to carbon disulfide ($CS_2$) and hydrogen ($H_2$) in the first reactor has a conversion rate of about 95%-100%, and a selectivity of the conversation to $CS_2$ of about 95%-100%.

6. The process of claim 1, wherein the second catalytic material comprises a $K_2O/NiMo/Al_2O_3$ catalyst; and the second feedstock comprises additional hydrogen ($H_2$) other than the resulted hydrogen ($H_2$) from the first reactor.

7. The process of claim 1, wherein the conversion of the carbon disulfide ($CS_2$) and hydrogen ($H_2$) to methanethiol ($CH_3SH$) and hydrogen sulfide ($H_2S$) in the second reactor has a conversion rate of about 80%-100%; and wherein the second reaction condition in the second reactor comprises a temperature in a range of about 200-600° C.; a pressure of about 1-3 bar; and an outlet temperature of the second reactor of about 400-500° C.

8. The process of claim 1, wherein the third catalytic material is a protonic zeolites H-ZSM-5 (Si/Al 15) catalyst.

9. The process of claim 1, wherein the third reaction condition in the third reactor comprises a temperature in a range of about 250-350° C.; a pressure of about 1-3 bar; and an outlet temperature of the third reactor of about 200-350° C.; and wherein the conversion of the methanethiol ($CH_3SH$) to the higher hydrocarbons in the third reactor has a high conversion rate of about 90-98%.

10. The process of claim 1, further comprising: supplying the third feedstock comprising the resulted methanethiol ($CH_3SH$) from step (iv) and the third catalytic material to a third economizer for a heat exchange before feeding to the third reactor; supplying water to the third economizer; conducting the heat exchange between the third feedstock and the water to reduce the temperature of the third feedstock to a range of about 250-350° C. and to heat up the water to form a steam; and supplying the third feedstock with reduced temperature from the third economizer to the third reactor.

11. The process of claim 10, further comprising: supplying a fourth feedstock comprising the resulted higher hydrocarbons from the third reactor to a fourth economizer for a heat exchange to form a final reaction mixture; supplying water to the fourth economizer; and conducting a heat exchange between the fourth feedstock and the water to reduce the temperature of the fourth feedstock to a range of about 25-150° C. and to heat up the water to a steam.

12. The process of claim 11, further comprising: supplying the resulted steam from the second, third and fourth economizers to the first economizer to pre-heat the first feedstock to up to about 900° C.

13. The process of claim 12, further comprising:
supplying the final reaction mixture to a propane cycle;
separating the final reaction mixture into bottom products and overhead products;
supplying the overhead products to an acid removal unit to remove at least a portion of the hydrogen sulfide to obtain a recovered mixture comprising recovered methane and recovered hydrogen sulfide; and
recycling the recovered mixture comprising back to the first economizer or to the first reactor,
wherein the final reaction mixture may comprise the higher hydrocarbons, methane, hydrogen sulfide, by products, and one or more of carbon disulfide ($CS_2$), hydrogen gas, methanethiol ($CH_3SH$) and liquid sulphur, wherein the bottom products at the bottom of the propane cycle comprises higher hydrocarbons including olefins and benzene, toluene and xylene, and wherein the overhead products of the propane cycle comprises methane and hydrogen sulfide.

14. A system for converting methane to higher hydrocarbons including olefins and aromatic hydrocarbons, the system comprising: a reaction unit comprising:
(i) a first reactor configured to receive a first feedstock, the first reactor comprising a first catalytic material formulated for converting at least a portion of the methane and hydrogen sulfide to carbon disulfide ($CS_2$) and hydrogen ($H_2$) to form a first resulted mixture comprising the carbon disulfide ($CS_2$) and the hydrogen ($H_2$);
(ii) a second reactor fluidly connected to the first reactor to receive the first resulted mixture, the second reactor comprising a second catalytic material formulated for converting at least a portion of the carbon disulfide ($CS_2$) and hydrogen ($H_2$) to methanethiol ($CH_3SH$) and hydrogen sulfide ($H_2S$) to form a second resulted mixture comprising the methanethiol ($CH_3SH$) and the hydrogen sulfide ($H_2S$);
(iii) a third reactor fluidly connected to the second reactor to receive the second resulted mixture, the third reactor comprising a third catalytic material formulated for converting at least a portion of the methanethiol ($CH_3SH$) to the higher hydrocarbons to produce a third resulted mixture comprising the higher hydrocarbons; and
a heat integration system comprising:
a first economizer configured to receive and preheat a first feedstock that feeds into the first economizer, the first economizer configured to be fluidly connected to the first reactor to supply the preheated first feedstock to the first reactor;
a fired heater configured to heat the first reactor;
a second economizer fluidly connected to the first reactor to receive and cool down the first resulted mixture from the first reactor, and fluidly connected to the second reactor to supply the cooled first resulted mixture to the second reactor;
a third economizer fluidly connected to the second reactor to receive and cool down the second resulted mixture from the second reactor; and fluidly connected to the third reactor configured to supply the cooled second resulted mixture to the third reactor; and
a fourth economizer fluidly connected to the third reactor to receive and cool down the third resulted mixture from the third reactor to form a final reaction mixture comprising the resulted higher hydrocarbons.

15. The system of claim 14, wherein the second, third and/or fourth economizers are configured to receive water and heat the water to form steam using heat energy generated in the first, second and third reactors respectively; and the first economizer is configured to receive the steam from the second, third and fourth economizers to preheat the first feedstock.

16. The system of claim 15, further comprising: a separation unit comprising a propane cycle fluidly connected to the fourth economizer, configured to receive and separate the final reaction mixture from the fourth economizer into bottom products and overhead products, the bottom products comprise the higher hydrocarbons and wherein the overhead products comprise methane and hydrogen sulfide.

17. The system of claim 16, further comprising: a recycling unit comprising an acid gas removal unit configured to receive the overhead products from the propane cycle and to remove at least a portion of the hydrogen sulfide to form a recovered mixture comprising the recovered methane and the recovered hydrogen sulfide in a weight ratio of about 1:1 to about 20:1; and recycling the recovered mixture from the acid gas removal unit to the first economizer.

* * * * *